US008272411B2

(12) United States Patent
Py

(10) Patent No.: US 8,272,411 B2
(45) Date of Patent: *Sep. 25, 2012

(54) LYOPHILIZATION METHOD AND DEVICE

(75) Inventor: Daniel Py, Larchmont, NY (US)

(73) Assignee: Medical Instill Technologies, Inc., New Milford, CT (US)

( * ) Notice: Subject to any disclaimer, the term of this patent is extended or adjusted under 35 U.S.C. 154(b) by 218 days.

This patent is subject to a terminal disclaimer.

(21) Appl. No.: 12/534,730

(22) Filed: Aug. 3, 2009

(65) Prior Publication Data

US 2010/0154245 A1    Jun. 24, 2010

Related U.S. Application Data

(63) Continuation of application No. 11/487,836, filed on Jul. 17, 2006, now Pat. No. 7,568,509, which is a continuation of application No. 10/833,371, filed on Apr. 28, 2004, now Pat. No. 7,077,176.

(60) Provisional application No. 60/465,992, filed on Apr. 28, 2003, provisional application No. 60/469,677, filed on May 12, 2003, provisional application No. 60/471,592, filed on May 19, 2003.

(51) Int. Cl.
*B65B 1/04* (2006.01)

(52) U.S. Cl. ............... 141/301; 141/351; 251/149.1; 251/149.7; 34/413; 34/417; 34/285; 34/381; 34/401

(58) Field of Classification Search .......... 141/346–352, 141/301, 302, 237; 251/149.1, 119.6, 149.7; 604/232, 197; 34/413, 417, 285, 287, 381, 34/559, 401
See application file for complete search history.

(56) References Cited

U.S. PATENT DOCUMENTS

| 1,471,091 | A | 10/1923 | Bessesen |
| 1,613,898 | A | 1/1927 | Metcalf et al. |
| 1,978,455 | A | 10/1934 | Geerlings |
| 2,128,035 | A | 8/1938 | Boetel |
| 2,186,908 | A | 1/1940 | Page et al. |
| 2,193,059 | A | 3/1940 | Chapman |
| 2,503,147 | A | 4/1950 | Applezweig |
| 2,667,986 | A | 2/1954 | Perelson |
| 2,842,276 | A | 7/1958 | Butler |

(Continued)

FOREIGN PATENT DOCUMENTS

CA    1123792    5/1982

(Continued)

OTHER PUBLICATIONS

International Search Report and Written Opinion issues by ISA/US in PCT/US04/12985.

(Continued)

*Primary Examiner* — Steven Douglas
(74) *Attorney, Agent, or Firm* — McCarter & English, LLP

(57) ABSTRACT

A lyophilization device configured for use in a lyophilization process has a body defining a chamber for receiving a liquid to be lyophilized, and a stopper creating a liquid-tight seal between the chamber and ambient atmosphere to form a sealed, empty sterile chamber. The stopper is adapted so that the chamber may be sterile filled with the substance through the stopper. A fluid passageway is formed through the stopper, through which the chamber is evacuated. The substance is lyophilized, the fluid passageway is closed, and the lyophilized substance is hermetically sealed within the chamber.

39 Claims, 28 Drawing Sheets

U.S. PATENT DOCUMENTS

| | | | |
|---|---|---|---|
| 3,092,278 A | 6/1963 | Jarnhall | |
| 3,136,440 A | 6/1964 | Krug et al. | |
| 3,193,128 A | 7/1965 | Ravn | |
| 3,235,128 A | 2/1966 | Hansen | |
| 3,261,694 A | 7/1966 | Forkner | |
| 3,278,063 A | 10/1966 | Kranzhoff | |
| 3,293,773 A | 12/1966 | Frazer et al. | |
| 3,340,671 A | 9/1967 | Loo | |
| 3,358,865 A | 12/1967 | Andersen | |
| 3,392,859 A | 7/1968 | Fischer | |
| 3,412,910 A | 11/1968 | Hahn | |
| 3,421,840 A | 1/1969 | Pechman | |
| 3,424,329 A | 1/1969 | Hersherg et al. | |
| 3,448,896 A | 6/1969 | Kobayashi et al. | |
| 3,454,178 A | 7/1969 | Bender et al. | |
| 3,637,102 A | 1/1972 | Shaw | |
| 3,648,903 A | 3/1972 | Marchant | |
| 3,669,323 A | 6/1972 | Harker et al. | |
| 3,685,248 A | 8/1972 | Godelaine | |
| 3,811,591 A | 5/1974 | Novitch | |
| 3,921,333 A | 11/1975 | Clendinning et al. | |
| 3,963,814 A | 6/1976 | Cospen et al. | |
| 3,993,069 A | 11/1976 | Buckles et al. | |
| 4,002,516 A | 1/1977 | Gaborieau et al. | |
| 4,023,607 A | 5/1977 | Jensen et al. | |
| 4,048,255 A | 9/1977 | Hillier et al. | |
| 4,084,330 A * | 4/1978 | Fraser | 34/92 |
| 4,102,476 A | 7/1978 | Loeffler | |
| 4,141,474 A | 2/1979 | Nilson | |
| 4,185,628 A | 1/1980 | Kopfer | |
| 4,205,754 A | 6/1980 | Nielsen et al. | |
| 4,233,262 A | 11/1980 | Curto | |
| 4,240,465 A | 12/1980 | Rader | |
| 4,250,611 A | 2/1981 | Wong | |
| 4,261,474 A | 4/1981 | Cohen | |
| 4,264,018 A | 4/1981 | Warren | |
| 4,265,364 A | 5/1981 | Baba | |
| 4,366,912 A | 1/1983 | Matukura et al. | |
| 4,390,111 A | 6/1983 | Robbins et al. | |
| 4,444,330 A | 4/1984 | Kasai et al. | |
| 4,456,138 A | 6/1984 | Bereziat | |
| 4,471,879 A | 9/1984 | Connor et al. | |
| 4,479,989 A | 10/1984 | Mahal | |
| 4,482,585 A | 11/1984 | Ohodaira et al. | |
| 4,499,148 A | 2/1985 | Goodale et al. | |
| 4,501,781 A | 2/1985 | Kushida et al. | |
| 4,510,169 A | 4/1985 | Linner | |
| 4,513,891 A | 4/1985 | Hain et al. | |
| D279,651 S | 7/1985 | Freeman | |
| 4,567,847 A | 2/1986 | Linner | |
| 4,578,295 A | 3/1986 | Jabarin | |
| 4,609,102 A | 9/1986 | Blum | |
| 4,615,963 A | 10/1986 | Matsumoto et al. | |
| 4,635,807 A | 1/1987 | Knapp | |
| 4,664,275 A | 5/1987 | Kasai et al. | |
| 4,664,277 A | 5/1987 | Connor | |
| 4,676,070 A | 6/1987 | Linner | |
| 4,682,703 A | 7/1987 | Kasai et al. | |
| 4,699,300 A | 10/1987 | Blake | |
| 4,703,781 A | 11/1987 | Meyer et al. | |
| 4,737,148 A | 4/1988 | Blake | |
| 4,739,906 A | 4/1988 | LoTurco | |
| 4,742,690 A | 5/1988 | Linner | |
| 4,745,771 A | 5/1988 | Linner | |
| 4,799,361 A | 1/1989 | Linner | |
| 4,815,619 A | 3/1989 | Turner et al. | |
| 4,834,149 A | 5/1989 | Fournier et al. | |
| 4,834,152 A | 5/1989 | Howson et al. | |
| 4,842,028 A | 6/1989 | Kaufman et al. | |
| 4,842,165 A | 6/1989 | Van Coney | |
| 4,865,871 A | 9/1989 | Livesey et al. | |
| 4,883,507 A | 11/1989 | Rey et al. | |
| 4,895,279 A | 1/1990 | Schultz | |
| 4,910,435 A | 3/1990 | Wakalopulos | |
| 4,923,480 A | 5/1990 | Monestere | |
| 4,949,877 A | 8/1990 | Hanna et al. | |
| 4,978,036 A | 12/1990 | Burd | |
| 4,981,464 A | 1/1991 | Suzuki | |
| 5,009,654 A | 4/1991 | Minshall et al. | |
| 5,024,830 A | 6/1991 | Linner | |
| 5,031,675 A | 7/1991 | Lindgren | |
| 5,033,647 A | 7/1991 | Smith et al. | |
| 5,038,839 A | 8/1991 | Morimoto et al. | |
| 5,046,645 A | 9/1991 | Hagan et al. | |
| 5,083,416 A | 1/1992 | Schneider et al. | |
| 5,085,332 A | 2/1992 | Gettig et al. | |
| 5,088,612 A | 2/1992 | Storar et al. | |
| 5,088,995 A | 2/1992 | Packard et al. | |
| 5,100,010 A | 3/1992 | Waters | |
| 5,108,007 A | 4/1992 | Smith et al. | |
| 5,129,212 A | 7/1992 | Duffey et al. | |
| 5,137,511 A | 8/1992 | Reynolds | |
| 5,178,300 A | 1/1993 | Haviv et al. | |
| 5,188,628 A | 2/1993 | Rani et al. | |
| 5,197,638 A | 3/1993 | Wood | |
| 5,215,538 A | 6/1993 | Larkin | |
| 5,226,568 A | 7/1993 | Newton et al. | |
| 5,247,015 A | 9/1993 | Bayan | |
| 5,318,204 A | 6/1994 | Davis et al. | |
| 5,320,256 A | 6/1994 | Wood | |
| 5,320,845 A | 6/1994 | Py | |
| 5,332,121 A | 7/1994 | Schmidt et al. | |
| 5,336,616 A | 8/1994 | Livesey et al. | |
| 5,339,972 A | 8/1994 | Crosnier et al. | |
| 5,340,541 A | 8/1994 | Jackson et al. | |
| 5,341,854 A | 8/1994 | Zezulka et al. | |
| 5,344,036 A | 9/1994 | Stanescu et al. | |
| 5,360,413 A | 11/1994 | Leason et al. | |
| 5,364,369 A | 11/1994 | Reynolds | |
| 5,366,108 A | 11/1994 | Darling | |
| 5,379,908 A | 1/1995 | Rohe | |
| 5,390,469 A | 2/1995 | Shimizu et al. | |
| 5,401,259 A | 3/1995 | Py | |
| 5,411,065 A | 5/1995 | Meador et al. | |
| 5,414,267 A | 5/1995 | Wakalopulos | |
| 5,416,303 A | 5/1995 | Grooms et al. | |
| 5,419,465 A | 5/1995 | Schroeder | |
| 5,423,791 A | 6/1995 | Bartlett | |
| 5,425,465 A | 6/1995 | Healy | |
| 5,429,254 A | 7/1995 | Christine | |
| 5,464,111 A | 11/1995 | Vacek et al. | |
| 5,484,566 A | 1/1996 | Gabbard | |
| 5,489,026 A | 2/1996 | D'Aloia | |
| 5,489,027 A | 2/1996 | Goerigk | |
| RE35,187 E | 3/1996 | Gortz | |
| 5,496,302 A | 3/1996 | Minshall et al. | |
| 5,497,910 A | 3/1996 | Meadows et al. | |
| RE35,203 E | 4/1996 | Wakalopulos | |
| D368,774 S | 4/1996 | Py | |
| 5,509,433 A * | 4/1996 | Paradis | 137/1 |
| 5,514,339 A | 5/1996 | Leopardi et al. | |
| 5,522,155 A | 6/1996 | Jones | |
| 5,549,141 A | 8/1996 | Meador et al. | |
| 5,556,678 A | 9/1996 | Jupin et al. | |
| D374,719 S | 10/1996 | Py | |
| 5,562,960 A | 10/1996 | Sugiura et al. | |
| 5,564,596 A | 10/1996 | Meadows et al. | |
| 5,565,160 A | 10/1996 | Makuuchi et al. | |
| 5,573,516 A | 11/1996 | Tyner | |
| 5,582,330 A | 12/1996 | Iba | |
| 5,596,814 A | 1/1997 | Zingle et al. | |
| 5,609,273 A | 3/1997 | Firestone et al. | |
| 5,612,588 A | 3/1997 | Wakalopulos | |
| 5,613,957 A | 3/1997 | Py | |
| 5,615,795 A | 4/1997 | Tipps | |
| 5,620,434 A | 4/1997 | Brony | |
| 5,641,004 A | 6/1997 | Py | |
| 5,650,192 A | 7/1997 | Britton et al. | |
| 5,656,498 A | 8/1997 | Iijima et al. | |
| D383,214 S | 9/1997 | Brennan | |
| 5,664,704 A | 9/1997 | Meadows et al. | |
| 5,673,535 A | 10/1997 | Jagger | |
| 5,676,267 A | 10/1997 | Slat et al. | |
| 5,676,346 A | 10/1997 | Leinsing | |
| 5,685,869 A | 11/1997 | Py | |
| 5,687,882 A | 11/1997 | Mueller | |
| 5,692,651 A | 12/1997 | Fuchs | |

| | | |
|---|---|---|
| 5,700,426 A | 12/1997 | Schmitthaeusler et al. |
| 5,702,019 A * | 12/1997 | Grimard ..................... 215/301 |
| D389,586 S | 1/1998 | Brennan |
| 5,718,334 A | 2/1998 | Demel |
| 5,718,348 A | 2/1998 | Manera |
| 5,727,333 A | 3/1998 | Folan |
| 5,727,892 A | 3/1998 | Baudin |
| 5,730,322 A | 3/1998 | Iba et al. |
| 5,732,837 A * | 3/1998 | Jones ......................... 215/311 |
| 5,743,441 A | 4/1998 | Baudin et al. |
| 5,744,087 A | 4/1998 | Williams et al. |
| 5,746,728 A | 5/1998 | Py |
| 5,759,218 A | 6/1998 | Martin et al. |
| 5,779,668 A | 7/1998 | Grabenkort |
| 5,780,130 A | 7/1998 | Hansen et al. |
| 5,780,295 A | 7/1998 | Livesey et al. |
| 5,799,837 A | 9/1998 | Firestone et al. |
| 5,803,311 A | 9/1998 | Fuchs |
| 5,804,236 A | 9/1998 | Frisk |
| 5,816,772 A | 10/1998 | Py |
| 5,823,373 A | 10/1998 | Sudo et al. |
| 5,823,397 A | 10/1998 | Gil |
| 5,837,193 A | 11/1998 | Childers et al. |
| 5,842,321 A | 12/1998 | Jones |
| 5,855,302 A | 1/1999 | Fisscher |
| 5,862,840 A | 1/1999 | Hansen |
| 5,871,110 A | 2/1999 | Grimard et al. |
| 5,871,908 A | 2/1999 | Henco et al. |
| 5,875,931 A | 3/1999 | Py |
| 5,876,372 A | 3/1999 | Grabenkort et al. |
| 5,879,345 A | 3/1999 | Aneas |
| 5,899,624 A | 5/1999 | Thompson |
| 5,902,298 A | 5/1999 | Niedospial, Jr. et al. |
| 5,909,032 A | 6/1999 | Wakalopulos |
| 5,921,989 A | 7/1999 | Deacon et al. |
| 5,927,550 A | 7/1999 | Mack et al. |
| 5,931,386 A | 8/1999 | Jouillat |
| 5,931,828 A | 8/1999 | Durkee |
| 5,934,500 A | 8/1999 | Cogger et al. |
| 5,937,536 A | 8/1999 | Kieselbach et al. |
| 5,944,702 A | 8/1999 | Py |
| 5,957,898 A | 9/1999 | Jepson et al. |
| 5,971,181 A | 10/1999 | Niedospial, Jr. et al. |
| RE36,410 E | 11/1999 | Meshberg |
| 6,003,702 A | 12/1999 | Grimard et al. |
| 6,006,932 A | 12/1999 | Morini |
| 6,021,824 A | 2/2000 | Larsen et al. |
| 6,029,946 A | 2/2000 | Doyle |
| 6,033,384 A | 3/2000 | Py |
| 6,050,435 A | 4/2000 | Bush et al. |
| 6,050,444 A | 4/2000 | Sugg |
| 6,053,370 A | 4/2000 | Ludbrook et al. |
| D425,205 S | 5/2000 | Henigan et al. |
| 6,058,625 A | 5/2000 | Kieselbach et al. |
| 6,062,430 A | 5/2000 | Fuchs |
| 6,062,437 A | 5/2000 | Mascitelli |
| 6,068,150 A | 5/2000 | Mitchell et al. |
| 6,070,623 A | 6/2000 | Aneas |
| 6,070,748 A | 6/2000 | Storar |
| 6,083,450 A | 7/2000 | Safian |
| 6,095,355 A | 8/2000 | Jessen et al. |
| 6,102,893 A | 8/2000 | Aneas |
| D430,939 S | 9/2000 | Zukor et al. |
| 6,135,172 A | 10/2000 | Fere et al. |
| 6,140,657 A | 10/2000 | Wakalopulos et al. |
| 6,145,688 A | 11/2000 | Smith |
| 6,145,707 A | 11/2000 | Baudin |
| 6,148,536 A | 11/2000 | Iijima |
| 6,158,146 A | 12/2000 | Kieselbach et al. |
| 6,168,037 B1 | 1/2001 | Grimard |
| 6,170,705 B1 | 1/2001 | Schneider et al. |
| 6,170,800 B1 | 1/2001 | Meloul et al. |
| 6,189,578 B1 | 2/2001 | Clusserath |
| 6,189,688 B1 | 2/2001 | Aneas |
| D439,345 S | 3/2001 | Herchenbach et al. |
| 6,199,350 B1 | 3/2001 | Brechel et al. |
| 6,202,901 B1 | 3/2001 | Gerber et al. |
| 6,223,918 B1 | 5/2001 | Browne |
| 6,234,335 B1 | 5/2001 | Gee et al. |
| 6,254,579 B1 | 7/2001 | Cogger et al. |
| 6,267,154 B1 | 7/2001 | Felicelli et al. |
| 6,267,768 B1 | 7/2001 | Deacon et al. |
| 6,283,976 B1 | 9/2001 | Portney |
| 6,290,680 B1 * | 9/2001 | Forsberg et al. ............... 604/232 |
| 6,301,767 B1 | 10/2001 | Granger et al. |
| 6,306,423 B1 | 10/2001 | Donovan et al. |
| 6,308,494 B1 | 10/2001 | Yuyama et al. |
| 6,312,708 B1 | 11/2001 | Donovan |
| RE37,471 E | 12/2001 | Jagger |
| 6,325,253 B1 | 12/2001 | Robinson |
| 6,343,711 B1 | 2/2002 | Coughlin |
| 6,343,713 B1 | 2/2002 | Abplanalp |
| 6,351,924 B1 | 3/2002 | Gustafsson et al. |
| 6,364,864 B1 | 4/2002 | Mohiuddin et al. |
| 6,382,441 B1 | 5/2002 | Carano |
| 6,383,509 B1 | 5/2002 | Donovan et al. |
| 6,385,943 B2 | 5/2002 | Yuyama et al. |
| 6,386,395 B1 | 5/2002 | Lunghetti |
| 6,428,545 B2 | 8/2002 | Portney |
| 6,446,844 B1 | 9/2002 | Gross |
| 6,447,498 B1 | 9/2002 | Jepson et al. |
| 6,450,994 B1 | 9/2002 | Boyles et al. |
| 6,478,788 B1 | 11/2002 | Aneas |
| 6,509,006 B1 | 1/2003 | Platz et al. |
| 6,541,802 B2 | 4/2003 | Doyle |
| 6,551,267 B1 * | 4/2003 | Cohen et al. .................. 604/6.15 |
| 6,564,471 B1 | 5/2003 | Sutherland et al. |
| 6,582,728 B1 | 6/2003 | Platz et al. |
| 6,604,561 B2 | 8/2003 | Py |
| 6,610,250 B1 | 8/2003 | Tuma |
| 6,649,267 B2 | 11/2003 | Agawa et al. |
| 6,662,977 B2 | 12/2003 | Gerber et al. |
| 6,684,916 B2 | 2/2004 | Py |
| 6,696,002 B1 | 2/2004 | Hekel |
| 6,726,389 B1 | 4/2004 | Lee |
| 6,797,258 B2 | 9/2004 | Platz et al. |
| 6,921,527 B2 | 7/2005 | Platz et al. |
| 6,929,040 B2 | 8/2005 | Py |
| 6,931,888 B2 | 8/2005 | Shekunov et al. |
| 6,962,006 B2 | 11/2005 | Chickering et al. |
| 6,984,395 B2 | 1/2006 | Boch et al. |
| 7,048,932 B2 | 5/2006 | Chow et al. |
| 7,073,349 B2 | 7/2006 | Shekunov et al. |
| 7,077,176 B2 | 7/2006 | Py |
| 7,097,827 B2 | 8/2006 | Platz et al. |
| 7,100,646 B2 | 9/2006 | Py |
| 7,112,341 B2 | 9/2006 | Nagarajan et al. |
| 7,141,547 B2 | 11/2006 | Rosen et al. |
| 7,186,241 B2 | 3/2007 | Py |
| 7,189,690 B2 | 3/2007 | Rosen et al. |
| 7,223,558 B2 | 5/2007 | Wu et al. |
| 7,238,660 B2 | 7/2007 | Rosen et al. |
| 7,238,667 B2 | 7/2007 | Rosen et al. |
| 7,456,256 B2 | 11/2008 | Wu et al. |
| 7,521,424 B2 | 4/2009 | Rosen et al. |
| 7,569,384 B2 | 8/2009 | Rosen et al. |
| 7,592,010 B2 | 9/2009 | Rosen et al. |
| 7,662,864 B2 | 2/2010 | Kanamathareddy et al. |
| 7,705,134 B2 | 4/2010 | Wu et al. |
| 7,765,713 B2 | 8/2010 | Ehrhard et al. |
| 7,799,759 B2 | 9/2010 | Rosen et al. |
| 7,847,079 B2 | 12/2010 | Rosen et al. |
| 7,966,746 B2 | 6/2011 | Py |
| 2001/0041872 A1 | 11/2001 | Paul, Jr. |
| 2001/0047154 A1 | 11/2001 | Jepson et al. |
| 2002/0006353 A1 | 1/2002 | Bilstad et al. |
| 2002/0010995 A1 | 1/2002 | Thibault et al. |
| 2002/0018731 A1 | 2/2002 | Bilstad et al. |
| 2002/0023893 A1 | 2/2002 | Sudo et al. |
| 2002/0029022 A1 | 3/2002 | Naritomi et al. |
| 2002/0056206 A1 | 5/2002 | Pace et al. |
| 2002/0131902 A1 | 9/2002 | Levy |
| 2002/0161334 A1 | 10/2002 | Castellano et al. |
| 2002/0172615 A1 | 11/2002 | Woodworth et al. |
| 2002/0193752 A1 | 12/2002 | Lynn |
| 2003/0035843 A1 | 2/2003 | Livesey et al. |
| 2003/0088216 A1 | 5/2003 | Py |
| 2003/0089743 A1 | 5/2003 | Py et al. |

| Publication No. | Date | Inventor |
|---|---|---|
| 2003/0143191 A1 | 7/2003 | Bell et al. |
| 2003/0156973 A1 | 8/2003 | Bilstad et al. |
| 2003/0157241 A1 | 8/2003 | Hossainy et al. |
| 2003/0159750 A1 | 8/2003 | Py |
| 2003/0178097 A1 | 9/2003 | Willstumpf |
| 2003/0195163 A1 | 10/2003 | Wu et al. |
| 2003/0222364 A1 | 12/2003 | Jackson et al. |
| 2003/0224014 A1 | 12/2003 | Chow et al. |
| 2003/0232359 A1 | 12/2003 | Ramanathan et al. |
| 2004/0002449 A1 | 1/2004 | Iruela-Arispe et al. |
| 2004/0009915 A1 | 1/2004 | Chang et al. |
| 2004/0030098 A1 | 2/2004 | Lee et al. |
| 2004/0118007 A1 | 6/2004 | Chickering et al. |
| 2004/0134091 A1 | 7/2004 | Chickering et al. |
| 2004/0137004 A1 | 7/2004 | Glenn et al. |
| 2004/0139624 A1 | 7/2004 | Chickering et al. |
| 2004/0154317 A1 | 8/2004 | Shekunov et al. |
| 2004/0208869 A1 | 10/2004 | Allan |
| 2004/0208870 A1 | 10/2004 | Allan |
| 2004/0256026 A1 | 12/2004 | Py |
| 2005/0048121 A1 | 3/2005 | East et al. |
| 2005/0048620 A1 | 3/2005 | Wu et al. |
| 2005/0054570 A1 | 3/2005 | Rosen et al. |
| 2005/0080136 A1 | 4/2005 | Watanabe et al. |
| 2005/0086830 A1 | 4/2005 | Zukor et al. |
| 2005/0175665 A1 | 8/2005 | Hunter et al. |
| 2005/0175703 A1 | 8/2005 | Hunter et al. |
| 2005/0178020 A1 | 8/2005 | Shekunov et al. |
| 2005/0178395 A1 | 8/2005 | Hunter et al. |
| 2005/0178396 A1 | 8/2005 | Hunter et al. |
| 2005/0178462 A1 | 8/2005 | Py |
| 2005/0182463 A1 | 8/2005 | Hunter et al. |
| 2005/0183731 A1 | 8/2005 | Hunter et al. |
| 2005/0186244 A1 | 8/2005 | Hunter et al. |
| 2005/0186664 A1 | 8/2005 | Rosen et al. |
| 2005/0187140 A1 | 8/2005 | Hunter et al. |
| 2005/0196421 A1 | 9/2005 | Hunter et al. |
| 2005/0208095 A1 | 9/2005 | Hunter et al. |
| 2006/0003367 A1 | 1/2006 | Wu et al. |
| 2006/0014254 A1 | 1/2006 | Haseltine et al. |
| 2006/0073162 A1 | 4/2006 | Chow et al. |
| 2006/0166364 A1 | 7/2006 | Senesac |
| 2006/0194735 A1 | 8/2006 | Rosen et al. |
| 2006/0210960 A1 | 9/2006 | Livesey et al. |
| 2006/0276396 A1 | 12/2006 | Rosen et al. |
| 2006/0286635 A1 | 12/2006 | Rosen et al. |
| 2007/0027306 A1 | 2/2007 | Rosen et al. |
| 2007/0048282 A1 | 3/2007 | Rosen et al. |
| 2007/0156102 A1 | 7/2007 | Py |
| 2007/0167853 A1 | 7/2007 | Melker et al. |
| 2007/0178088 A1 | 8/2007 | Wu et al. |
| 2007/0203448 A1 | 8/2007 | Melker et al. |
| 2007/0208134 A1 | 9/2007 | Hunter et al. |
| 2007/0224128 A1 | 9/2007 | Dennis et al. |
| 2007/0244047 A1 | 10/2007 | Rosen et al. |
| 2007/0259815 A1 | 11/2007 | Rosen et al. |
| 2007/0292941 A1 | 12/2007 | Handique et al. |
| 2007/0299043 A1 | 12/2007 | Hunter et al. |
| 2008/0004206 A1 | 1/2008 | Rosen et al. |
| 2008/0028632 A1 | 2/2008 | Py |
| 2008/0039773 A1 | 2/2008 | Py |
| 2008/0057004 A1 | 3/2008 | Bell et al. |
| 2008/0071063 A1 | 3/2008 | Allan et al. |
| 2008/0095806 A1 | 4/2008 | Bathurst et al. |
| 2008/0112972 A1 | 5/2008 | Truong-Le |
| 2008/0146503 A1 | 6/2008 | Rosen et al. |
| 2008/0153751 A1 | 6/2008 | Rosen et al. |
| 2008/0161243 A1 | 7/2008 | Rosen et al. |
| 2008/0167238 A1 | 7/2008 | Rosen et al. |
| 2008/0167239 A1 | 7/2008 | Rosen et al. |
| 2008/0167240 A1 | 7/2008 | Rosen et al. |
| 2008/0194481 A1 | 8/2008 | Rosen et al. |
| 2008/0213886 A1 | 9/2008 | Rosen et al. |
| 2008/0229609 A1 | 9/2008 | Bronshtein |
| 2008/0234652 A1 | 9/2008 | McCarthy et al. |
| 2008/0234653 A1 | 9/2008 | McCarthy et al. |
| 2008/0234654 A1 | 9/2008 | McCarthy et al. |
| 2008/0276482 A1 | 11/2008 | Broughall et al. |
| 2008/0293629 A1 | 11/2008 | Rosen et al. |
| 2009/0029914 A1 | 1/2009 | Rosen et al. |
| 2009/0047358 A1 | 2/2009 | Weers et al. |
| 2009/0053238 A1 | 2/2009 | Allan |
| 2009/0088385 A1 | 4/2009 | Wu et al. |
| 2009/0093402 A1 | 4/2009 | Rosen et al. |
| 2009/0099073 A1 | 4/2009 | Rosen et al. |
| 2009/0107001 A1 | 4/2009 | McCarthy |
| 2009/0113753 A1 | 5/2009 | Pepper et al. |
| 2009/0158612 A1 | 6/2009 | Thilly et al. |
| 2009/0258850 A1 | 10/2009 | Frincke et al. |
| 2010/0048472 A1 | 2/2010 | Rosen et al. |
| 2010/0093627 A1 | 4/2010 | Rosen et al. |
| 2010/0129316 A1 | 5/2010 | Levitt |
| 2010/0152410 A1 | 6/2010 | East et al. |
| 2010/0154245 A1 | 6/2010 | Py |
| 2010/0254944 A1 | 10/2010 | Subramanian et al. |
| 2010/0254985 A1 | 10/2010 | Allan et al. |
| 2010/0286791 A1 | 11/2010 | Goldsmith |
| 2010/0291033 A1 | 11/2010 | Rosen et al. |
| 2010/0297231 A1 | 11/2010 | Vehring et al. |
| 2010/0317518 A1 | 12/2010 | Stevens et al. |
| 2011/0002888 A1 | 1/2011 | Rosen et al. |
| 2011/0009312 A1 | 1/2011 | Rosen et al. |
| 2011/0020947 A1 | 1/2011 | Bedingham et al. |
| 2011/0253250 A1 | 10/2011 | Py |

FOREIGN PATENT DOCUMENTS

| | | |
|---|---|---|
| EP | 0802827 | 8/1998 |
| EP | 0649795 | 6/1999 |
| EP | 960623 A2 | 12/1999 |
| EP | 0673852 | 2/2000 |
| EP | 0 921 151 | 10/2001 |
| FR | 2509689 | 7/1981 |
| GB | 500534 | 2/1939 |
| GB | 984149 | 2/1965 |
| GB | 2026995 A | 2/1980 |
| GB | 2091229 | 7/1982 |
| GB | 2364700 | 2/2002 |
| JP | 06211645 A | 8/1994 |
| JP | 07165252 A | 6/1995 |
| JP | 10165480 A | 6/1998 |
| JP | 10234822 A | 9/1998 |
| JP | 2002220344 A | 8/2002 |
| WO | WO 95/34381 | 12/1995 |
| WO | WO 96/06018 | 2/1996 |
| WO | WO 9720181 A1 | 6/1997 |
| WO | WO 9918402 A1 | 4/1999 |
| WO | WO 2007/038773 A1 | 4/2007 |
| WO | WO 2007/127286 A2 | 11/2007 |

OTHER PUBLICATIONS http://www.bio-set.com/htm/InstUseInj.htm, printed Mar. 20, 2003.
http://www.bio-set.com/htm/IntroductionInj.htm, printed Mar. 20, 2003.
http://www.bio-set.com/htm/Choice.htm, printed Mar. 20, 2003.
http://www.bio-set.com/htm/EndUserBenef.htm, printed Mar. 20, 2003.
http://www.bio-set.com/htm/specinj.htm, printed Mar. 20, 2003.
http://www.bio-set.com/htm/IntroductionInf.htm, printed Mar. 20, 2003.
http://www.bio-set.com/htm/InstUseInf.htm, printed Mar. 20, 2003.
http://www.bio-set.com/htm/SpecInf.htm, printed Mar. 20, 2003.

* cited by examiner

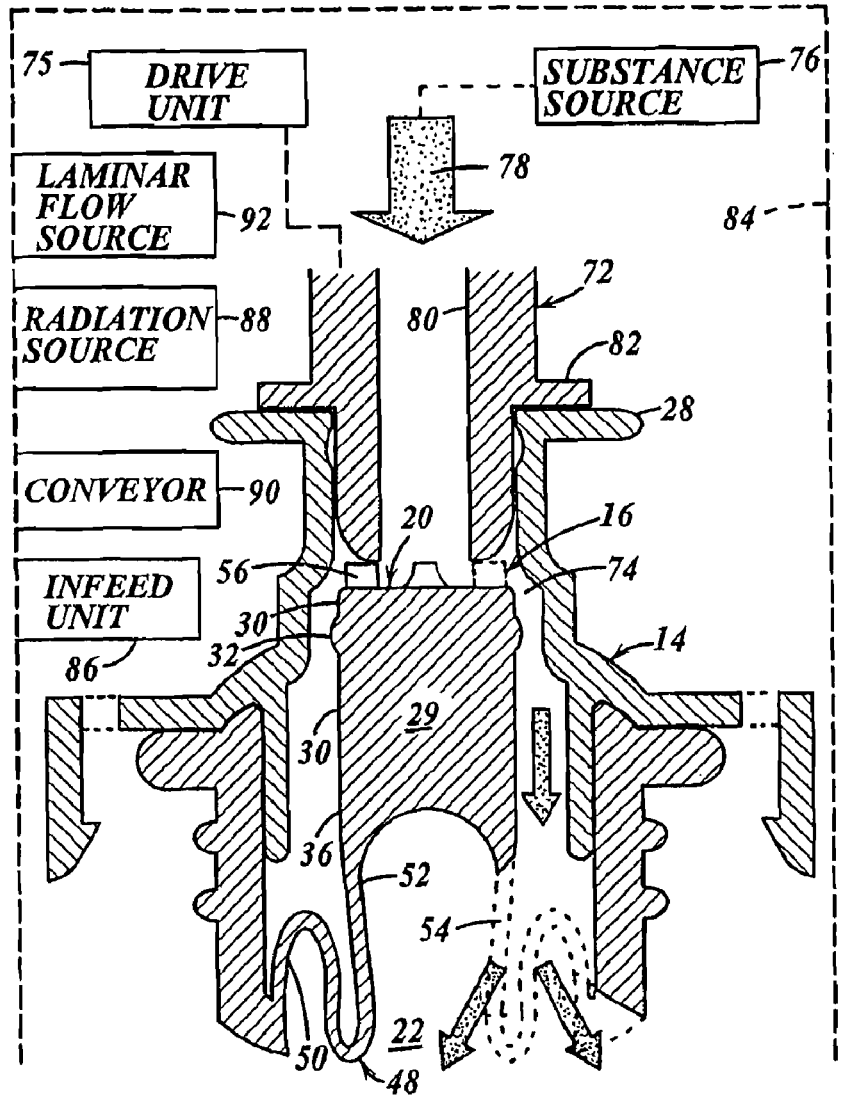

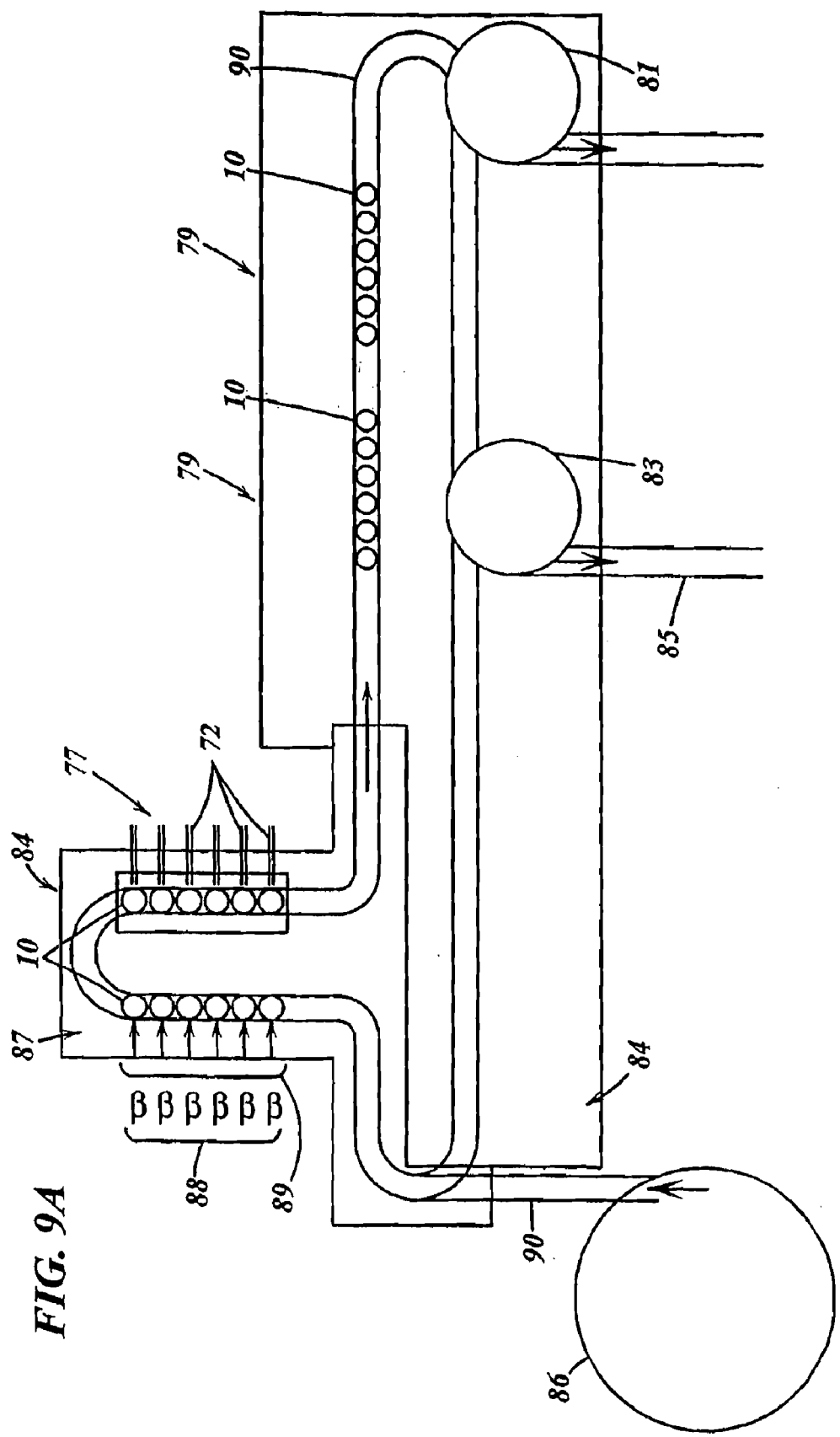

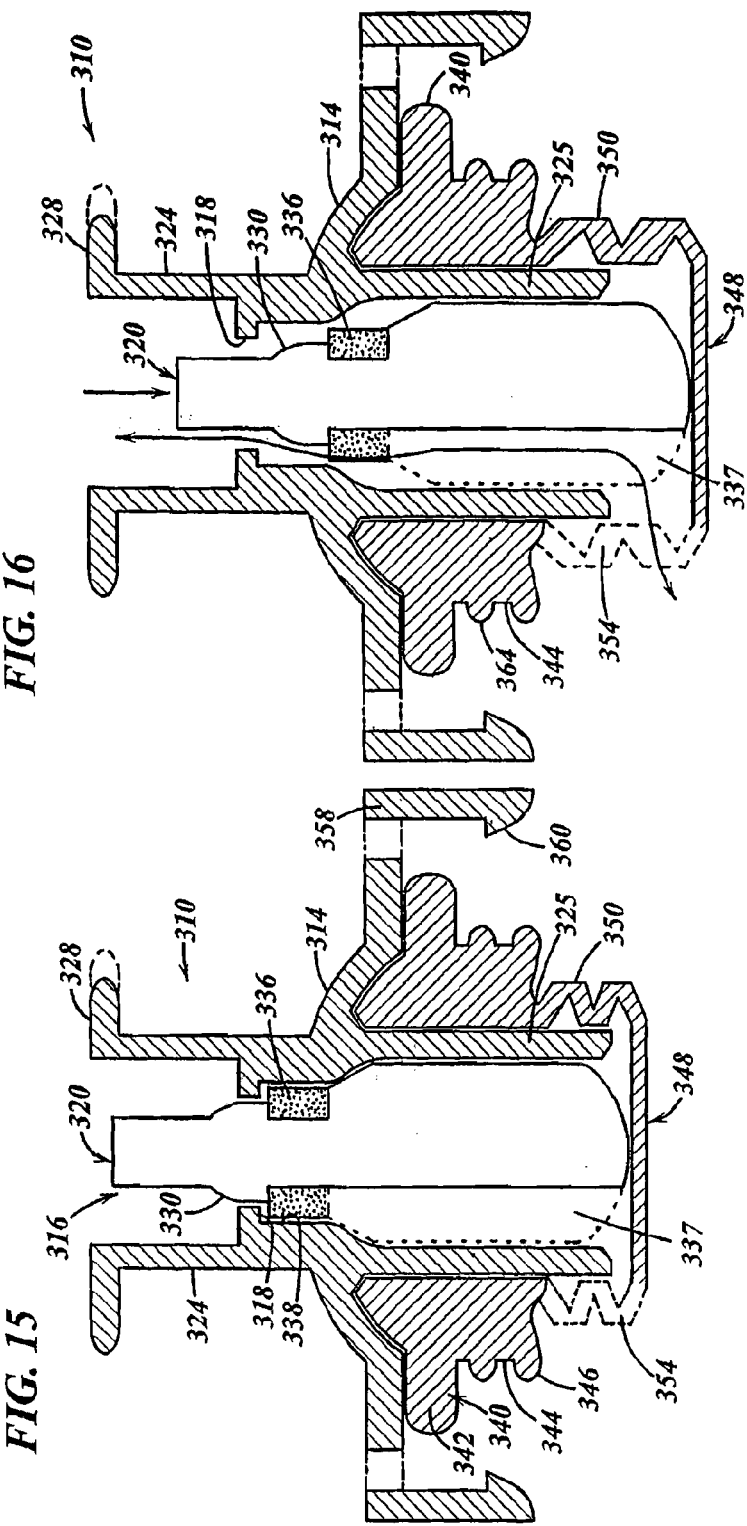

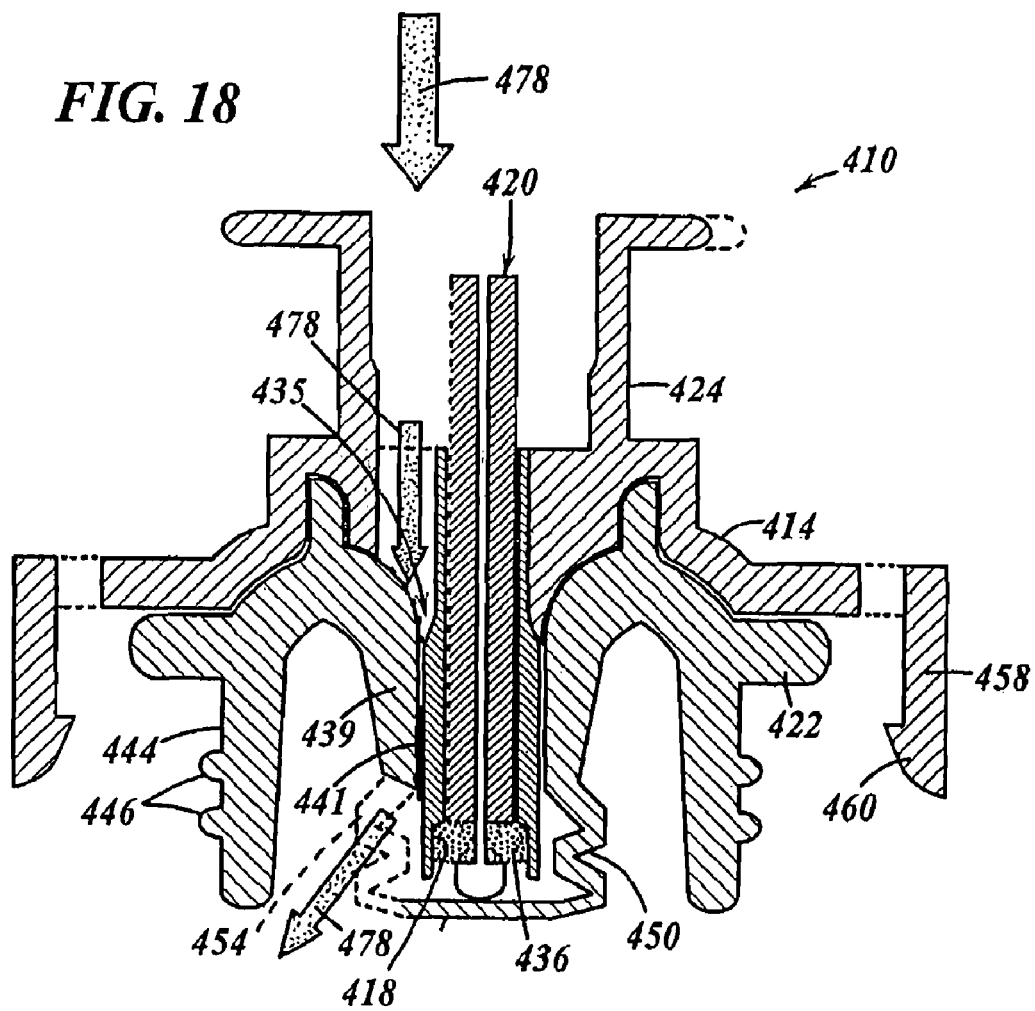

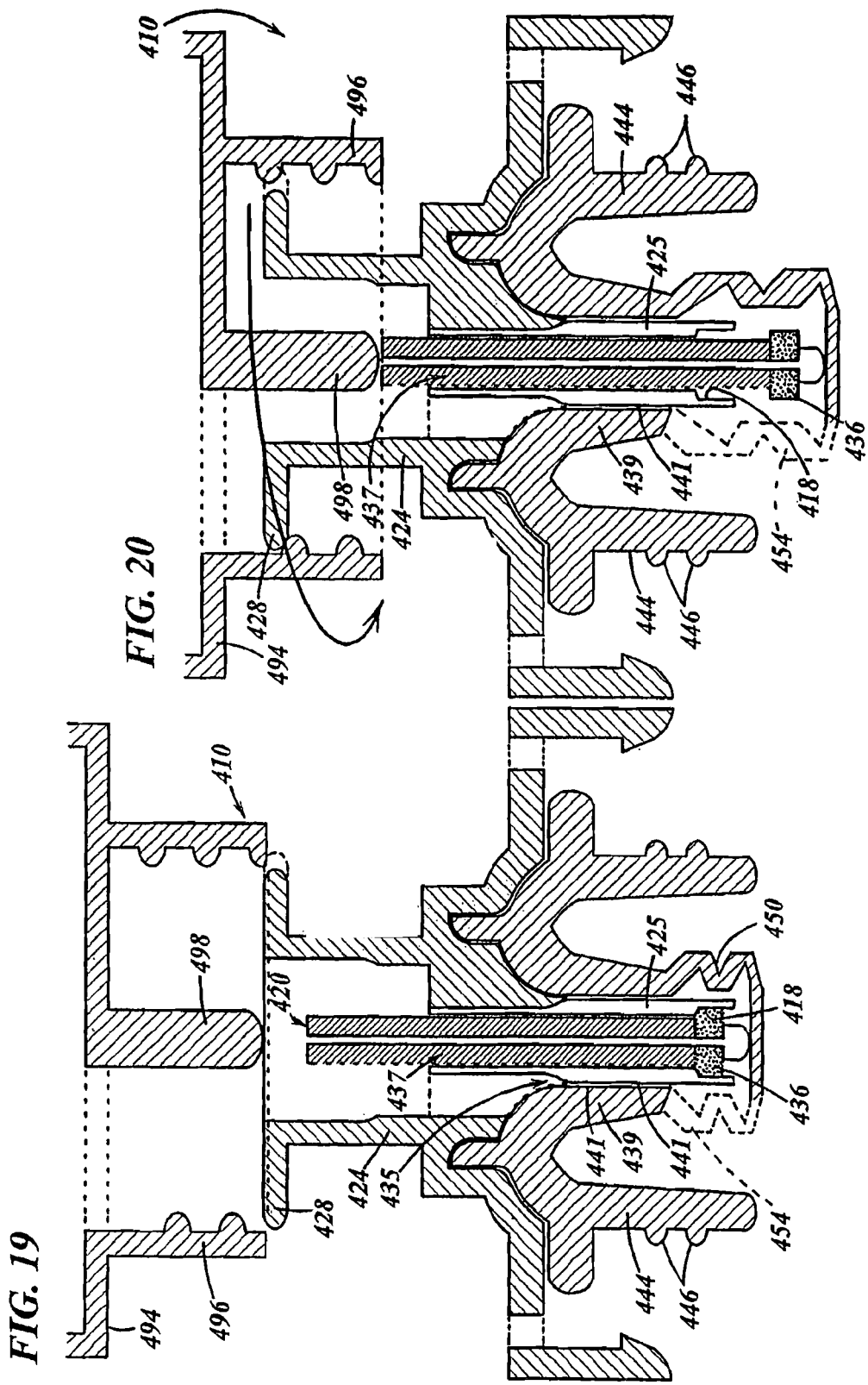

LYOPHILIZATION METHOD AND DEVICE

CROSS-REFERENCE TO RELATED PRIORITY APPLICATIONS

This patent application is a continuation of U.S. patent application Ser. No. 11/487,836, filed Jul. 17, 2006 entitled "Container with Valve Assembly and Apparatus and Method for Filling," now U.S. Pat. No. 7,568,509, issued Aug. 4, 2009, which is a continuation of U.S. patent application Ser. No. 10/833,371, filed Apr. 28, 2004 entitled "Container with Valve Assembly for Filling and Dispensing Substances, and Apparatus and Method for Filling," now U.S. Pat. No. 7,077,176, issued Jul. 18, 2006, claiming benefit of U.S. Application Ser. No. 60/465,992, filed Apr. 28, 2003, entitled "Container with Valve Assembly for Filling and Dispensing Substances, and Apparatus and Method for Filling," U.S. Application Ser. No. 60/469,677, filed May 12, 2003, entitled "Dispenser and Apparatus and Method for Filling a Dispenser," and U.S. Application Ser. No. 60/471,592, filed May 19, 2003, entitled "Dispenser and Apparatus and Method for Filling a Dispenser." Each of the foregoing applications are hereby expressly incorporated by reference as part of the present disclosure as if fully set forth herein.

BACKGROUND OF THE INVENTION

1. Field of the Invention

The present invention relates to devices and methods for lyophilizing a liquid that has been filled into a container that is sealed, particularly vials, dispensers, and other containers for medicaments and other substances.

2. Background Information

Sterile filling of medicament containers or dispensers, such as vials, is a relatively complex and expensive process. Commercially available medicament vials include a glass or plastic vial and a rubber stopper. Prior to filling, the vials and stoppers are typically washed, sterilized, such as by the application of radiation thereto, or autoclaved, and then filled and assembled in sterilized isolators.

An improvement to such prior art systems is disclosed in U.S. Pat. No. 6,684,916, entitled "Medicament Vial Having a Heat-Sealable Cap, and Apparatus and Method for Filling the Vial,", U.S. application Ser. No. 10/766,172 (U.S. Pat. No. 7,032,631), entitled "Medicament Vial Having a Heat-Sealable Cap, and Apparatus and Method for Filling the Vial," and in U.S. application Ser. No. 10/655,455 (U.S. Pat. No. 7,100,646), entitled "Sealed Containers and Methods of Making and Filling Same," each of which is assigned to the assignee of the present invention and is hereby expressly incorporated by reference as part of the present disclosure as if fully set forth herein. The apparatus and methods disclosed in these co-pending applications involve vials including resealable stoppers, wherein a sealed empty vial is sterilized, such as by applying radiation thereto, the stopper is penetrated by a needle or like injection member to fill the empty, sterilized vial with a medicament or other substance to be contained therein, and then the needle hole in the stopper is re-sealed by applying thermal energy, such as with a laser beam, thereto.

Although the vials with resealable stoppers can provide significant advantages with respect to cost savings, simplicity, and sterility assurance in comparison to prior art vial and stopper assemblies, they require needle penetration and resealing of the stoppers. Also, many current vial and stopper assemblies do not permit mechanical connection to a syringe such that the same vial can be used to provide multiple doses of medicaments or other substances contained therein.

Accordingly, it is an object of the present invention to overcome one or more of the drawbacks and disadvantages of prior vials and stoppers or vial and stopper assemblies.

SUMMARY OF THE INVENTION

In accordance with a first aspect, a device fillable in a filling assembly includes a filling member coupled in fluid communication with a substance source for introducing the substance into the device. The device comprises a body defining a chamber for receiving a substance therein, and a valve assembly connectable in fluid communication between the filling member and the chamber for introducing the substance through the valve assembly and into the chamber. The valve assembly includes an axially-extending valve seat, and a flexible valve member overlying the valve seat. The flexible valve member and the valve seat form a normally closed interface defining a fluid-tight seal therebetween. The flexible valve member is flexible outwardly relative to the valve seat in response to the introduction of substance at sufficient pressure from the filling member into the interface between the valve member and the valve seat to open the valve assembly and allow passage of the substance therethrough and into the chamber.

The valve assembly may define an annular, axially-extending interface between the valve member and the valve seat. The valve seat is relatively rigid in comparison to the valve member, and the valve member is relatively flexible in comparison to the valve seat. The relatively flexible valve member extends about a periphery of the relatively rigid valve seat. Preferably, the valve member forms an interference fit with the valve seat at the interface of the valve member and the valve seat to thereby form the fluid-tight seal therebetween. The valve member may define a progressively decreasing wall thickness in an axial direction toward the chamber. Also, the flexible valve member may extend annularly about the valve seat, and forms a normally closed annular seam at the interface of the valve member and the valve seat for allowing the passage of substance at sufficient pressure therethrough. The valve assembly may include a body defining an inlet port connectable in fluid communication with the filling member, and a plurality of inlet apertures in fluid communication between the inlet port and the interface of the valve member and the valve seat.

The filling member may define a tubular conduit for the passage of the substance therethrough, and is movable into engagement with the valve assembly for introducing the substance from the tubular conduit through the valve assembly and into the chamber.

The axially-extending valve seat and flexible valve cover may form an inlet valve for introducing the substance through the inlet valve and into the chamber, and the valve assembly further includes an outlet valve that is normally closed and forms a fluid-tight seal between the chamber and ambient atmosphere. The outlet valve includes a valve member and a valve seat, the valve member engages the valve seat in the normally closed position defining a fluid-tight seal therebetween, and the valve member is movable relative to the valve seat to allow the passage of fluid from the chamber between the valve member and valve seat.

In accordance with another aspect, a device fillable in a filling assembly may include a filling member coupled in fluid communication with a substance source for introducing the substance into the device. The device comprises a body defining a chamber for receiving a substance therein, and first means connectable in fluid communication between the filling member and the chamber for introducing the substance through the first means and into the chamber. The first means includes second means extending axially within the first means and cooperating with third means for forming a normally closed interface between the second and third means defining a fluid-tight seal. The first means further includes third means cooperating with the second means for forming the normally closed interface defining the fluid-tight seal, and for flexing outwardly relative to the second means in response to the introduction of substance at sufficient pressure from the filling member into the interface between the second and third means to allow passage of the substance through the interface and into the chamber.

The first means further may include fourth means for cooperating with fifth means for forming a normally closed interface between the fourth and fifth means and defining a fluid-tight seal between the chamber and ambient atmosphere. The first means further includes fifth means cooperating with the fourth means for forming the normally closed interface defining the fluid-tight seal, and for moving relative to the fourth means to allow the passage of fluid from the chamber between the fourth and fifth means.

The first means may be a valve assembly, the second means may be a valve seat, the third means may be a valve member, the fourth means may be a valve seat, and the fifth means may be a valve member.

In accordance with another aspect, there is a method of filling a device with a substance, wherein the device includes a body defining a chamber for receiving the substance therein, and a valve assembly including an axially-extending valve seat, and a flexible valve member overlying the valve seat and forming a normally closed interface defining a fluid-tight seal between the valve member and the valve seat. The method comprises the following steps:

(i) providing a device having a sealed, empty sterile chamber;

(ii) filling the sterile empty chamber with the substance by moving at least one of the valve assembly and a filling member into fluid communication with the other;

(iii) introducing the substance from the filling member at sufficient pressure into the interface between the valve member and the valve seat to flex the valve member outwardly relative to the valve seat and, in turn, flow through the interface between the valve member and the valve seat and into the chamber;

(iv) terminating the flow of the substance from the filling member into the interface between the valve member and the valve seat, allowing the flexible valve member to form the normally closed interface defining the fluid-tight seal between the valve member and the valve seat, and in turn sealing the substance with the chamber; and (v) moving at least one of the valve assembly and the filling member relative to the other to disconnect the valve assembly and the filling member from fluid communication with each other.

The method may further comprise the step of sterilizing the sealed, empty device. The sterilizing step may include irradiating the sealed empty device. The step of irradiating the sealed empty device may include subjecting the device to gamma, e-beam and/or laser radiation.

The method may further comprise the step of providing a device having a valve assembly wherein the axially-extending valve seat and flexible valve cover form an inlet valve for introducing the substance through the inlet valve and into the chamber, and the valve assembly further includes an outlet valve that is normally closed and forms a fluid-tight seal between the chamber and ambient atmosphere. The method may further comprise the step of dispensing substance from the chamber through the outlet valve. The dispensing step may include dispensing multiple doses of the substance from the chamber through the outlet valve, and maintaining the substance remaining within the chamber after each dose sterile and sealed within the chamber with respect to the ambient atmosphere.

In a still further aspect, a lyophilization device is provided. The device has a body defining a sealed, empty sterile chamber, and a stopper forming a liquid-tight seal between the chamber and ambient atmosphere. The stopper is adapted for sterile filling a liquid substance to be lyophilized through the stopper and into the sealed, empty, sterile chamber. A fluid passageway through the stopper may be formed, so that the chamber may be evacuated through the fluid passageway of the stopper, and the substance within the evacuated chamber may be lyophilized. The fluid passageway through the stopper may be closed and the lyophilized substance within the chamber hermetically sealed therein.

In a method of lyophilization, a sealed empty sterile device is provided, which has a body defining a chamber and a stopper forming a liquid-tight seal between the chamber and ambient atmosphere. A liquid substance to be lyophilized is sterile-filled into chamber through the stopper. A fluid passageway is formed through the stopper and the chamber is evacuated through the stopper, and then the substance in the evacuated chamber is lyophilized. The fluid passageway through the stopper is closed and the lyophilized substance in the chamber is hermetically sealed therein.

Advantageously, the container and stopper may be assembled and sterilized empty, and then the empty sterilized assembly may be filled with a sterile substance, such as a medicament. This may be accomplished by filling through the one-way valve or other mechanism forming a fluid passageway. As a result, the container and stopper assemblies may be sterile filled at a significantly lesser cost than prior art vial and stopper assemblies, and can provide significantly improved levels of sterility assurance. Yet another advantage is that the vial, other container or dispenser of the present invention can hold multiple doses of the substance to be contained therein, such as a medicament, including, for example, a vaccine or an injectable fluid, and can dispense multiple doses therefrom. Other objects and advantages of the present invention will become apparent in view of the following detailed description of embodiments of the invention taken in conjunction with the accompanying drawings.

BRIEF DESCRIPTION OF THE DRAWINGS

FIG. 9 is a partial, cross-sectional, somewhat schematic view of the vial assembly of FIG. 1 mounted in an apparatus for filling the vial and showing the filling member of the apparatus depressing the valve member to move same from the closed to the open position and, in turn, introduce a fluid or other substance through the valve and into the chamber of the vial;

FIG. 9A is a somewhat schematic, top plan view of a sterile filling assembly for use in filling the vial assemblies;

FIG. 15 is a partial, cross-sectional, somewhat schematic view of another vial assembly wherein the valve assembly includes a bellows-shaped spring;

FIG. 16 is a partial, cross-sectional, somewhat schematic view of the vial assembly of FIG. 15 showing the valve assembly in the open position for introducing substance into and/or withdrawing substance from the vial;

FIG. 18 is a partial, cross-sectional, somewhat schematic view of the vial assembly of FIG. 17 showing the flow of substance into the vial for filling the vial;

FIG. 19 is a partial, cross-sectional, somewhat schematic view of the vial assembly of FIG. 17 showing the connection of a syringe to the vial assembly;

FIG. 20 is a partial, cross-sectional, somewhat schematic view of the vial assembly of FIG. 17 showing the syringe fully connected to the vial for withdrawing substance from the vial, through the valve assembly, and into the syringe;

DETAILED DESCRIPTION OF EMBODIMENTS OF THE INVENTION

Figure 1:
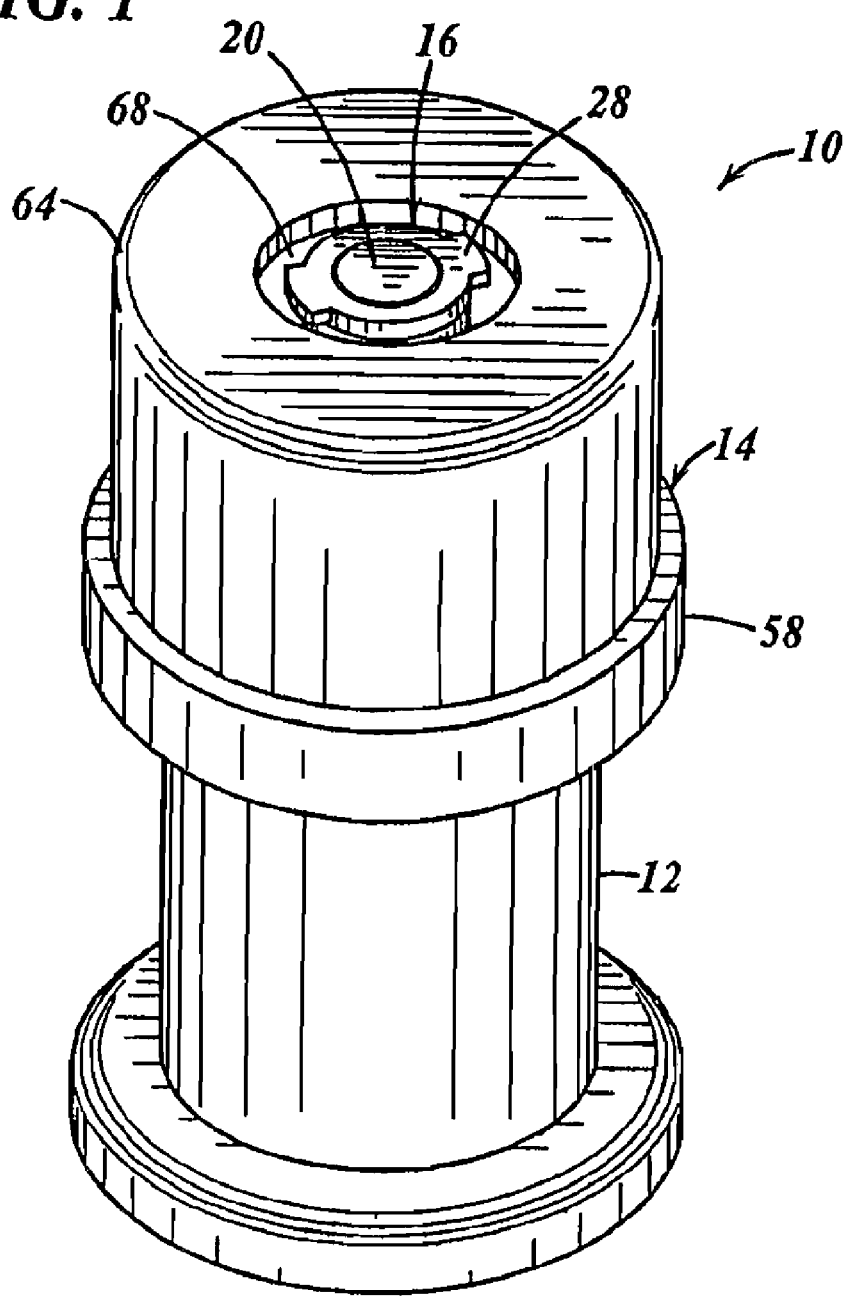
FIG. 1 is a perspective view of a vial assembly that includes a valve assembly for filling the vial assembly and dispensing fluids or other substances therefrom.
Figure 2:
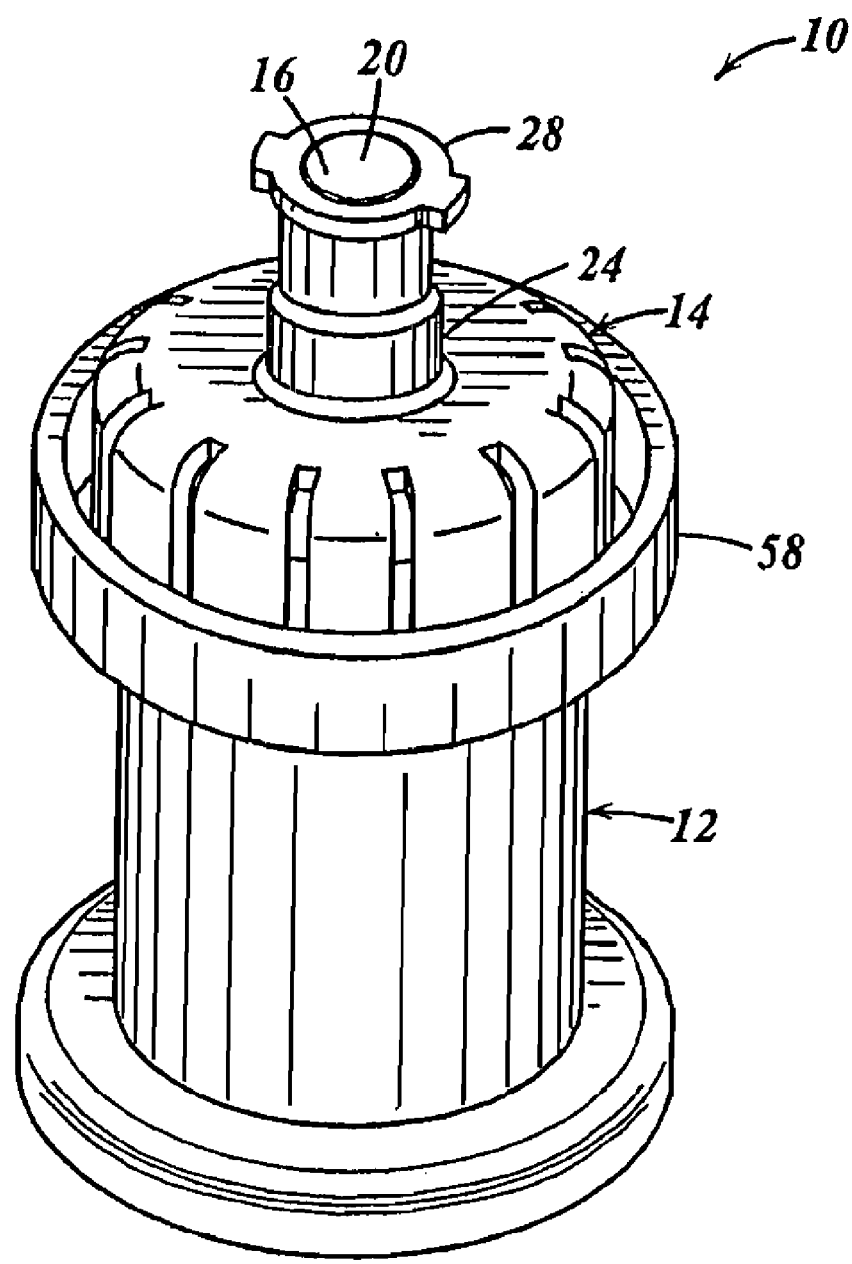
FIG. 2 is a perspective view of the vial assembly of FIG. 1 with the cover removed and showing the cap and valve assemblies in further detail.
Figure 3:
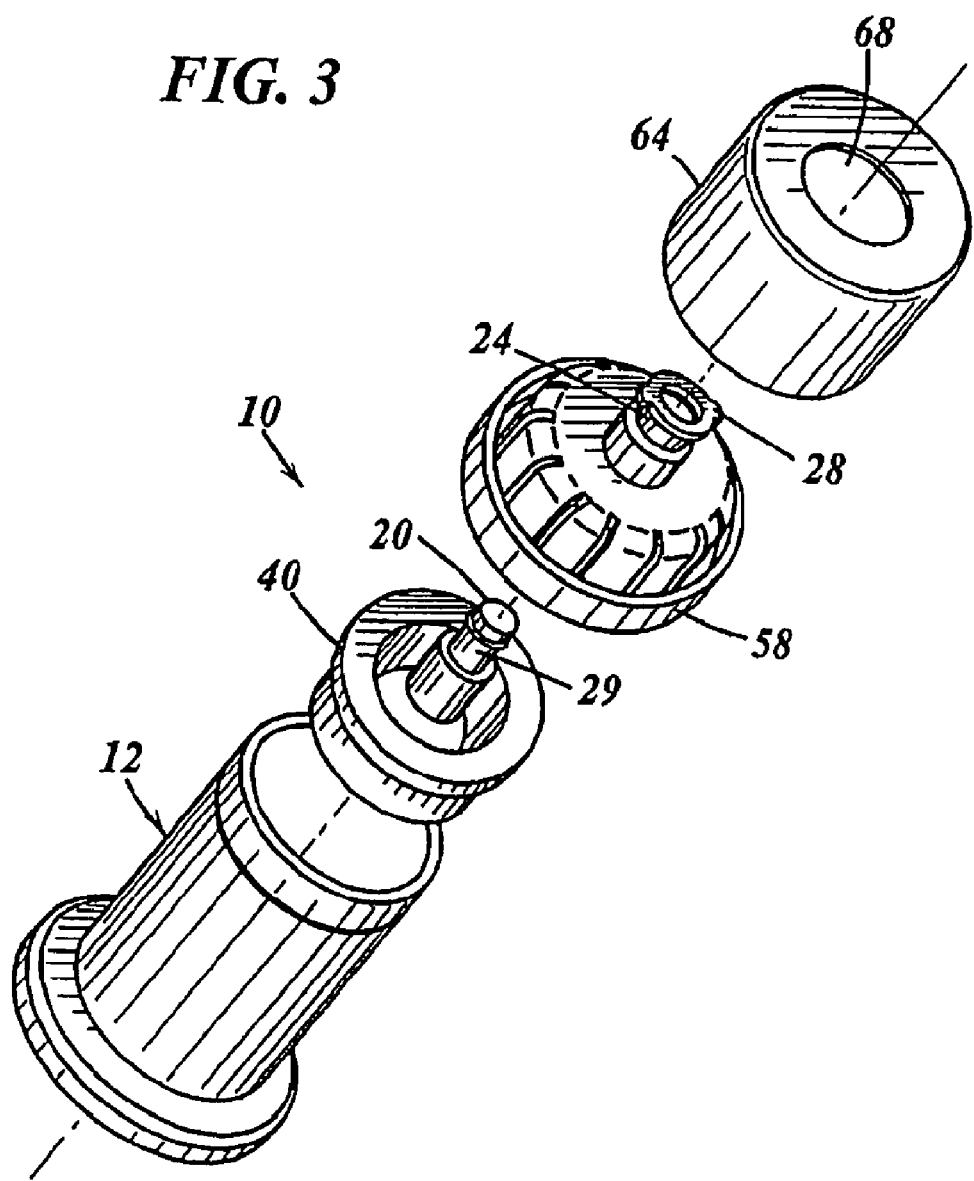
FIG. 3 is an exploded view of the vial assembly of FIG. 1.
Figure 4:
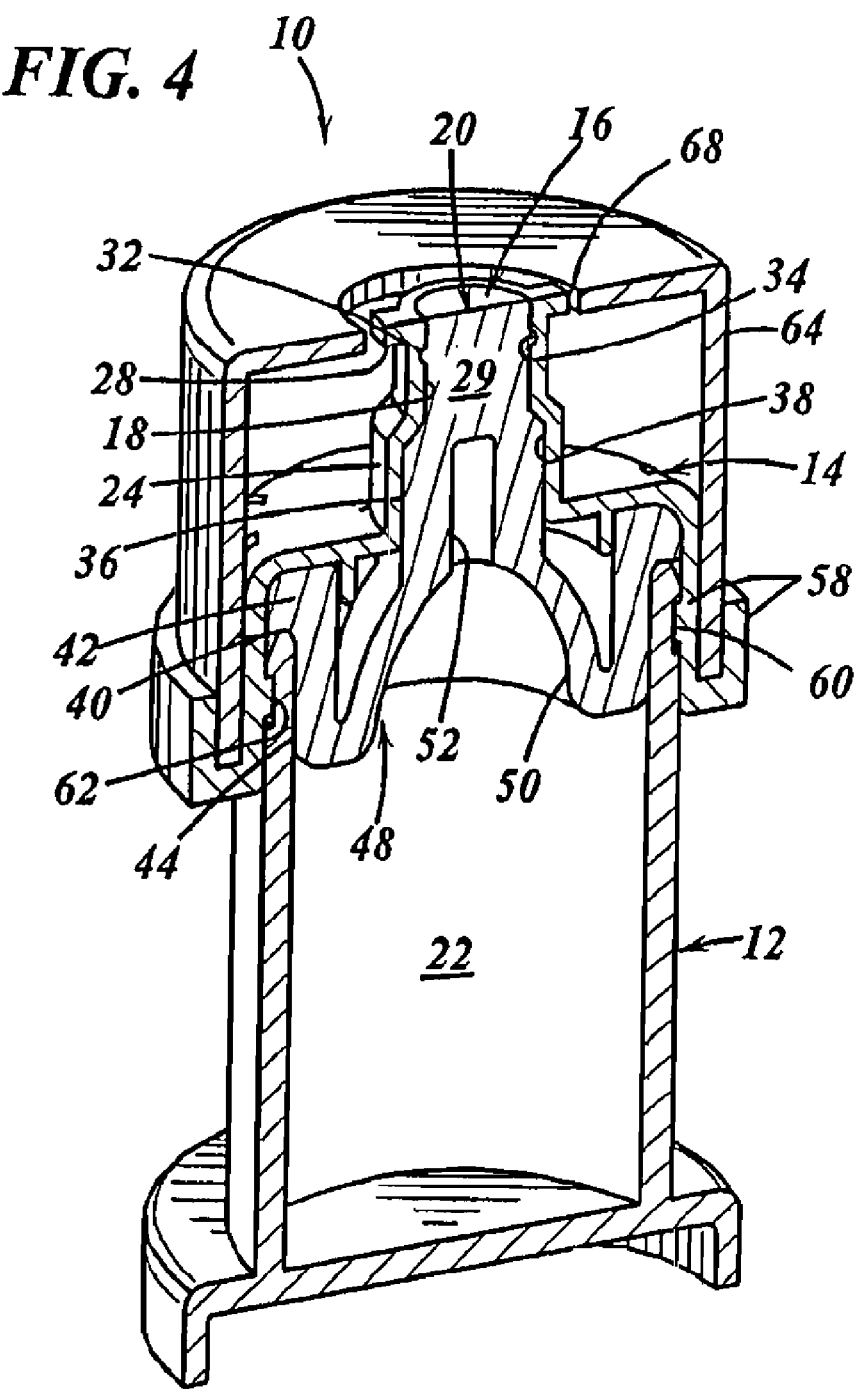
FIG. 4 is a cross-sectional, perspective view of the vial assembly of FIG. 1.
Figure 5:
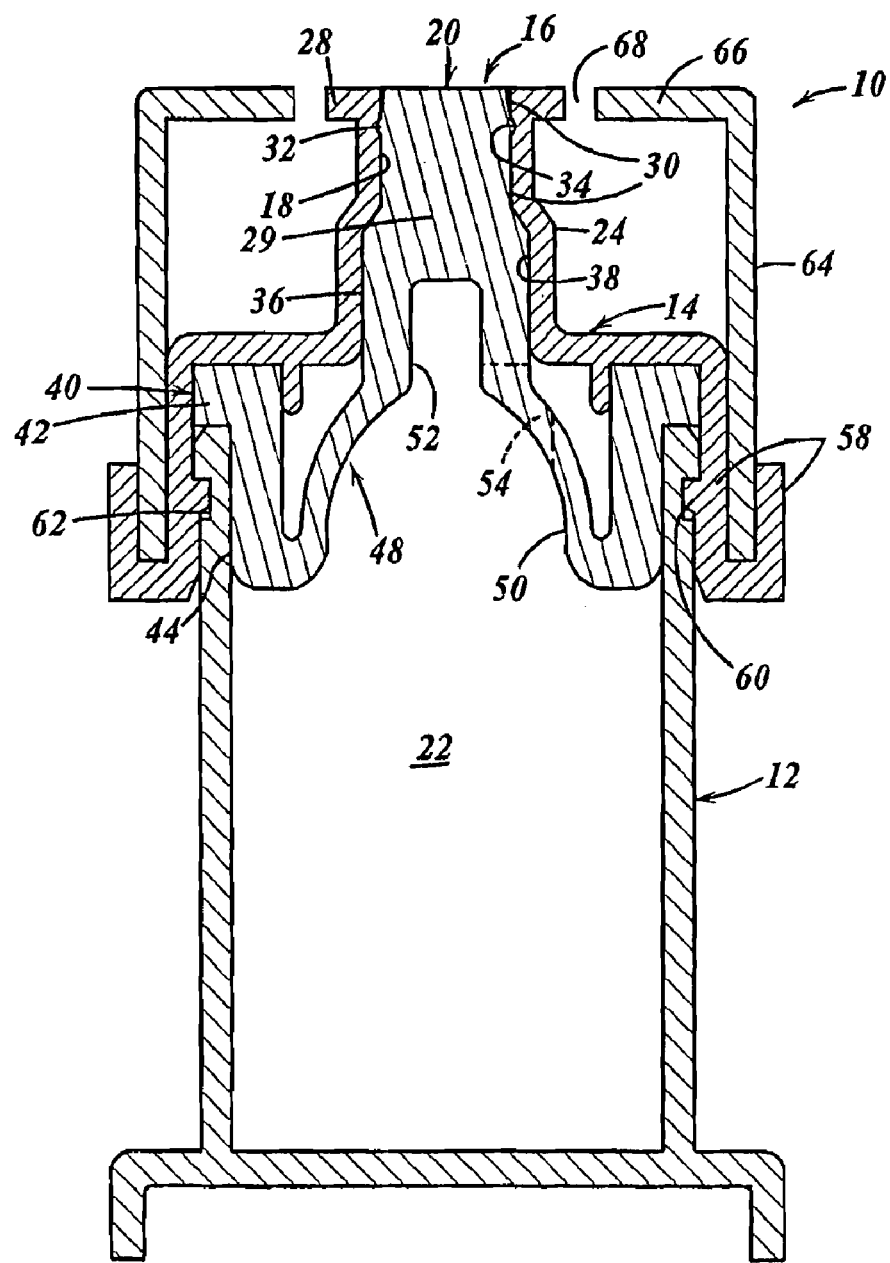
FIG. 5 is another cross-sectional view of the vial assembly of FIG. 1.
Figure 6:
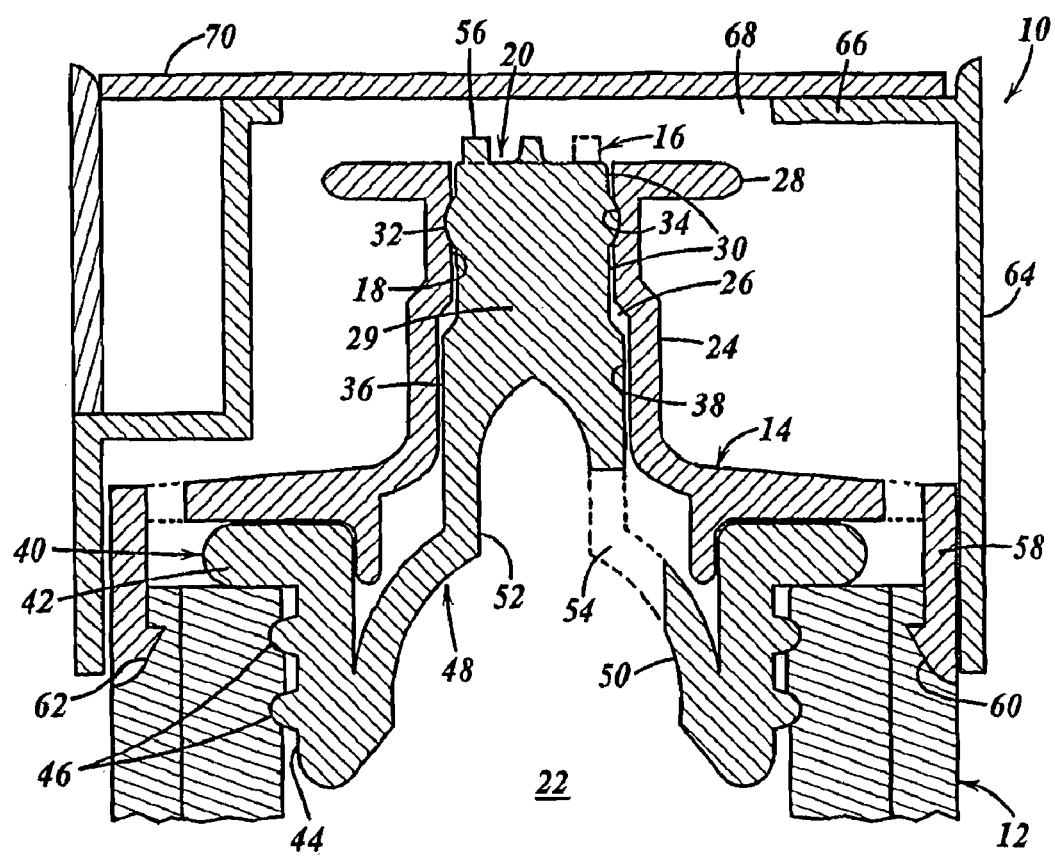
FIG. 6 is partial, cross-sectional, somewhat schematic view of the vial assembly of FIG. 1.
Figure 8:
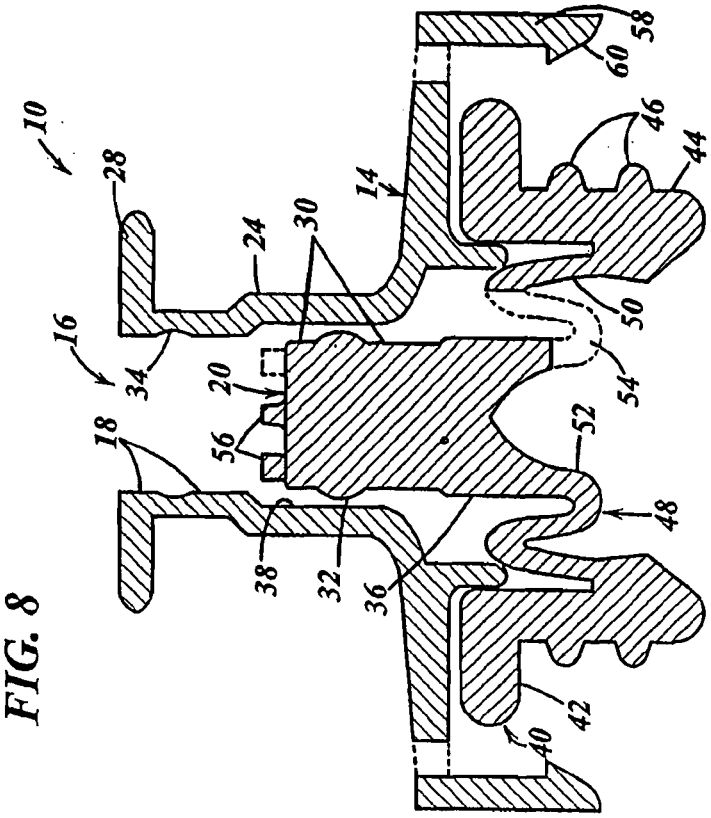
FIG. 8 is a view similar to that of FIG. 7 but showing the valve in the open position.
Figure 7:
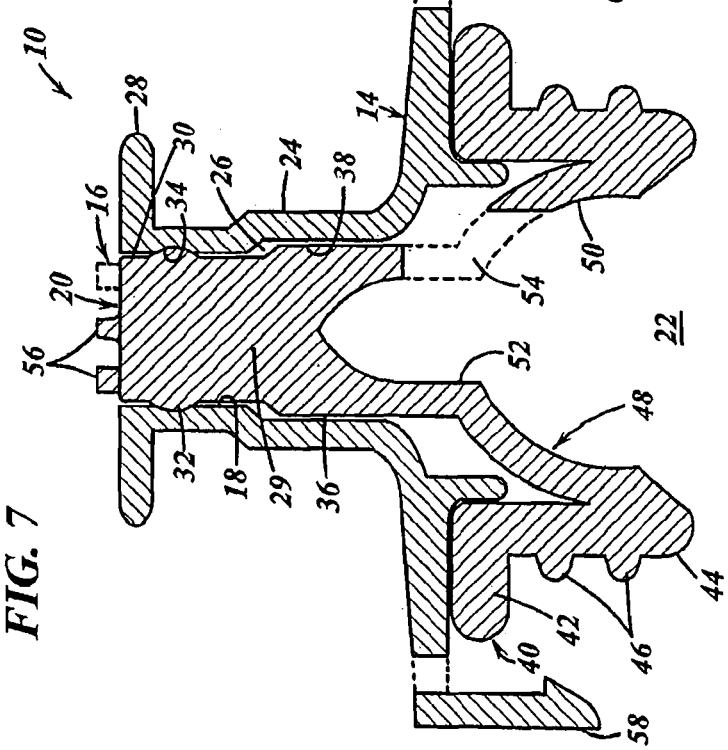
FIG. 7 is a partial, cross-sectional, somewhat schematic view of the vial assembly of FIG. 1 with some parts removed and illustrating the valve in the closed position.
Figure 10:
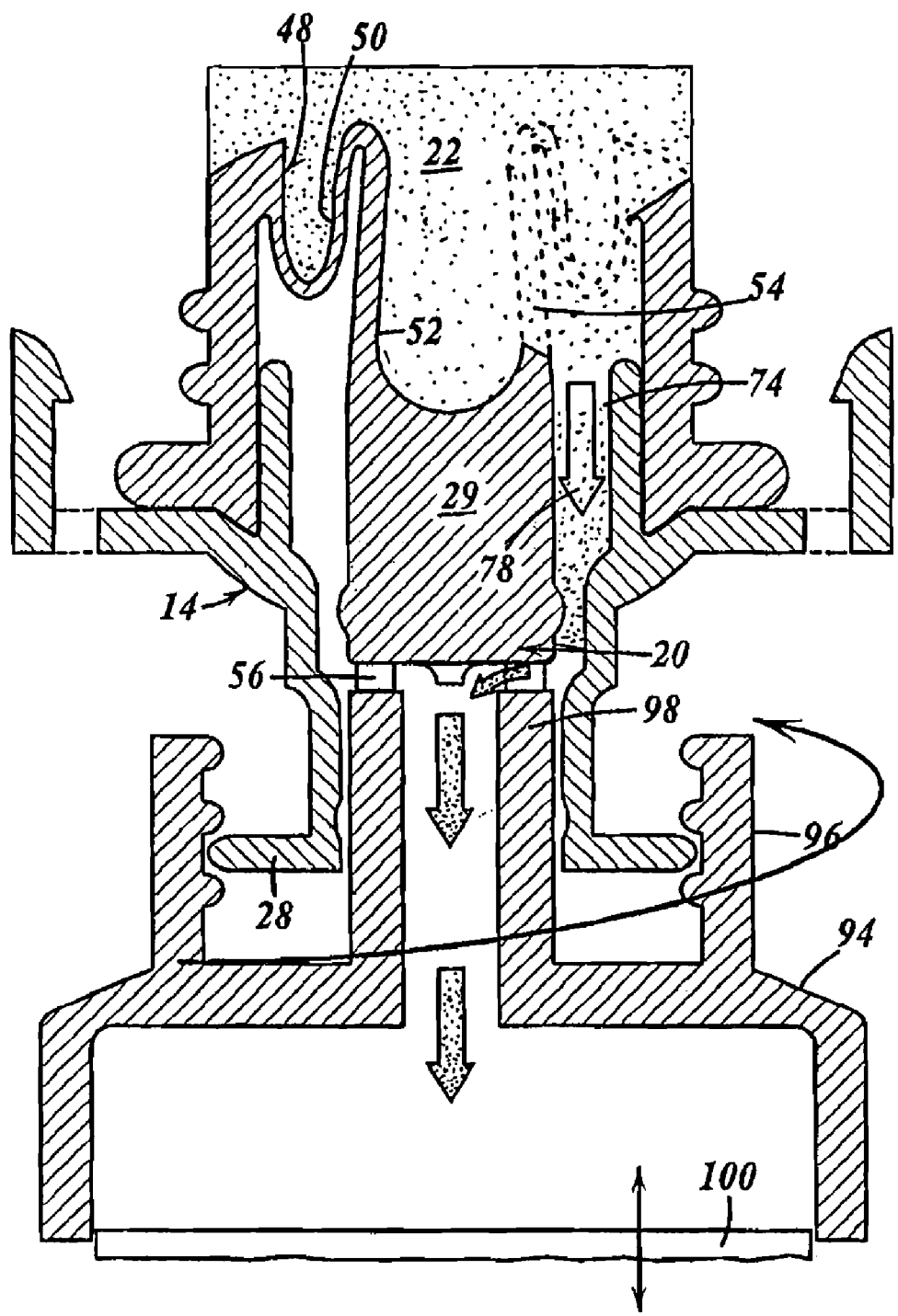
FIG. 10 is a partial, cross-sectional, somewhat schematic view of the vial assembly of FIG. 1 releasably connected to a syringe for opening the valve upon connecting the syringe to the vial and withdrawing fluid or other substance in the chamber of the vial through the open valve and into the syringe by actuating the plunger of the syringe and, in turn, sealing the remaining fluid within the vial upon disconnecting the syringe and vial and allowing the valve to return to its normally closed position.

In FIG. 1 a vial assembly is indicated generally by the reference numeral 10. The vial assembly 10 includes a body 12, a cap assembly 14 and a valve assembly 16 mounted within the cap assembly. As shown in FIGS. 4-8, the valve assembly 16 includes a valve seat 18 and a flexible valve member 20. The body 12 defines a chamber 22 coupled in fluid communication with the valve assembly 16. As described in further detail below, the flexible valve member 20 is movable between a closed position, as shown in FIGS. 4-7, wherein the flexible valve member 20 sealingly engages the valve seat 18 to form a fluid-tight seal therebetween and hermetically seal a substance contained within the chamber 22 within the vial, and an open position, as shown in FIGS. 8-10, wherein the valve member 20 is moved out of engagement with the valve seat 18 to define an opening therebetween and, in turn, permit the passage of substance through the valve assembly to both introduce the substance into the chamber 22 and the dispensing of the substance therefrom.

The cap assembly 14 includes a hub 24 defining an axially-extending passageway 26 therein for receiving the flexible valve member 20 and forming on its interior surface the valve seat 18. A vial mounting surface 28 is formed about the periphery of the hub 24 and, as described further below, is adapted to threadedly engage the mounting portion of a syringe to connect the vial to the syringe (FIG. 10). The valve member 20 defines in an upper portion 29 thereof a first annular sealing surface 30 that engages the valve seat 18 in the closed position to form a fluid-tight seal therebetween. The flexible valve member 20 further defines a raised annular lobe 32 that is received within a corresponding annular recess 34 formed in the valve seat 18 to releasably retain the valve member in the closed position. The flexible valve member 20 further defines a second annular sealing surface 36 that is axially spaced relative to the first annular sealing surface 30 and sealingly engages a corresponding annular sealing surface 38 formed on the interior of the hub 24. As can be seen, the second annular sealing surface 38 defines a larger diameter (or width) than the first annular sealing surface 30 to form an open passageway between the valve member and valve seat when in the open position.

The valve member 20 further defines a base portion 40 including a peripheral flange 42 that sealingly engages the outer edge of the body 12, and an annular sealing surface 44 that sealingly engages the inner wall of the body 12 to form a fluid-tight seal therebetween. If desired, the annular sealing surface 44 may include a plurality of annular ribs 46 to facilitate forming a fluid-tight seal. The base portion 40 of the flexible valve member 20 further defines an integral spring 48 that allows the flexible valve member 20 to move axially between the closed and open positions, and normally biases the valve member into the closed position. As illustrated, the spring 48 includes an approximately dome or spherical-shaped portion 50 formed at the base, and a hollow substantially cylindrical shaped portion 52 extending axially between the dome-shaped portion 50 and the annular sealing surfaces 30 and 36. An aperture 54 is formed through the flexible valve member 20 at the juncture of the dome-shaped portion 50 and cylindrical-shaped portion 52 to allow the flow of substance therethrough when the valve is in the open position. As may be recognized by those of ordinary skill in the pertinent art based on the teachings herein, the valve member 20 may include any desired number of flow apertures 54, and the flow apertures may take any of numerous different configurations in order to, for example, achieve the desired flow of substances into and/or out of the chamber of the vial.

The flexible valve member 20 may define on its exterior end a plurality of nubs or other protuberances 56 radially spaced relative to each other for engaging a filling member (FIG. 9) to move the valve member between the closed and open positions, to permit the flow of substance between the filling member and the valve member, and to facilitate the flow of fluid through the valve member and into a syringe, as described further below. As illustrated in the drawings, the nubs 50 are not always required. Rather, the nubs may be eliminated where unnecessary to obtain proper flow of fluid or other substance through the valve either from the filling member into the vial, or from the vial into a syringe.

The flexible valve member 20 is preferably made of a resilient polymeric material that is compatible with the substance to be contained within the vial, and exhibits appropriate physical properties for purposes of storing the substance and otherwise performing the functions of the valve member as described herein. The thermoplastic material may be a blend of a first material that is preferably a styrene block copolymer, such as the materials sold under either the trademarks KRATON or DYNAFLEX, and a second material that is preferably an olefin, such as the materials sold under either the trademarks ENGAGE or EXACT. The first and second materials may be blended within the range of about 50:50 by weight to about 90:10 by weight (i.e., first material:second material). The benefits of described blend over the first material by itself are improved water or vapor barrier properties, and thus improved product shelf life; a reduced coefficient of friction; improved moldability or mold flow rates; and a reduction in hystereses losses. Alternatively, the flexible valve member 20 may be formed of KRATON itself, or of a vulcanized rubber. As may be recognized by those skilled in the pertinent art based on the teachings herein, these materials and blends of materials are only exemplary, and any of numerous different materials or blends of materials that are currently or later become known for performing the functions of the flexible valve member equally may be employed.

The cap assembly 14 includes a peripheral flange 58 defining on an interior surface thereof a raised annular surface 60 that is received within a corresponding annular recess 62 of the body 12 to fixedly secure the cap to the body. As can be seen, the raised annular surface 60 defines a curvilinear chamfer on its interior surface to permit the flange 58 of the cap to be axially slipped onto the open end of the vial body and snapped into the recess 62 to fixedly secure the cap to the body. As also shown, the peripheral flange 42 of the flexible valve member 20 is compressed between the cap 14 and body 12 to form a fluid-tight seal therebetween.

The vial assembly 10 further includes a protective cover 64 that is fixedly secured to the flange 58 of the cap assembly and/or body 12, such as by an adhesive, ultrasonic welding, snap-fit, or any of numerous different fastening mechanisms that are currently known, or later become known for performing this function. The cover 64 defines in its upper wall 66 an aperture 68 for allowing access therethrough to the valve assembly 16. As shown typically in FIG. 6, a tamper proof sealing member 70 is preferably releasably secured to the upper wall 66 after filling the vial with the substance to be contained therein to prevent tampering during transportation and storage. The tamper proof seal 70 may take the form of any of numerous such devices that are currently or later become known for performing this function, such as an adhesive-backed foil that is releasably secured to the upper wall 66 of the cover.

In the operation of the vial 10, as shown in FIG. 9, the vial is filled by moving a filling member 72 axially into engagement with the nubs 56 formed on the exterior surface of the flexible valve member 20 to, in turn, depress with the filling member 72 the valve member 20 axially inwardly into the vial from the closed to the open position. As can be seen, upon moving the valve member 20 axially inwardly, the upper portion 29 of the valve member is pressed axially inwardly into the base portion 40 such that the dome-shaped spring portion 50 moves laterally outwardly and the hollow cylindrical portion 52 moves axially inwardly and outwardly. This, in turn, allows the upper portion 29 of the valve to move inwardly and the sealing surfaces 30 and 36 thereof to move away from the corresponding sealing surfaces 18 and 38, respectively, and define a valve opening 74 therebetween (FIG. 9). In the open position, and as illustrated by the arrows in FIG. 9, the substance is permitted to flow from the filling member 72, through the valve opening 74, through the aperture 54 in the valve member 20, and into the chamber 22 of the body 12.

The filling member 72 may take the form of any of numerous different types of filling members that are currently or later become known for performing the function of the filling member as disclosed herein. For example, the filling member can define more than one flow path for simultaneously introducing the substance from the filling member into the chamber of the vial and withdrawing gas therefrom. In this instance, the filling member is connected to a vacuum source for creating a suction within the flow path and withdrawing gas from the chamber 22 therethrough. As shown in FIG. 9, the filling member 72 is drivingly connected to a drive unit 75 for moving the filling member into and out of engagement with the valve member 20. The filling member 72 also is coupled in fluid communication with a substance source 76 that contains the substance 78 to be introduced through the filling member and into the vial. Preferably, the substance source 76 includes one or more pumps for pumping the substance 78 through the filling member and into the vial. The filling member 72 defines a conduit 80 for introducing the substance 78 therethrough, and a peripheral lip 82 for contacting the mounting surface 28 of the vial.

Upon filling the chamber 22 to the desired level, the filling member 72 is then moved axially by the drive unit 75 away from the valve member 20 to, in turn, allow the spring 48 to drive the valve member axially outwardly and move the sealing surfaces 30 and 36 into sealing engagement with the corresponding surfaces 18 and 38, respectively, of the valve seat. Once the raised annular surface 32 of the valve member is received within the corresponding recess 34 of the valve seat 18, the valve member 20 is releasably secured in the closed position.

One of the advantages of the illustrated example is that the substantially dome-shaped or concave-shaped spring portion 48 creates a substantial spring force to move the valve member 20 from the open to the closed position, and to cause the sealing surfaces of the valve member to sealingly engage the valve seat and form a fluid-tight seal therebetween. As may be recognized by those of ordinary skill in the pertinent art based on the teachings herein, the spring portion 48 of the valve member 20 may take any of numerous different shapes and/or configurations, or may be formed of any of numerous different materials, that are currently, or later become known for performing the function of the spring as described herein. For example, the spring may define a shape other than a dome shape, or may not be formed integral with the valve member. Also, the shape and/or material of construction of the spring may be selected to control the spring force applied to the valve member. One advantage of the substantially dome-shaped configuration, however, is that the dome shape imparts lateral (or radial) and axial forces to the valve member 20 to facilitate maintaining a fluid-tight seal throughout the shelf-life and usage of the container 10.

As illustrated in FIGS. 9 and 9A, the filling of the vials is preferably performed in a sterile filling assembly including a sterile enclosure 84 and a laminar flow source 92 (not shown in FIG. 9A) for providing a substantially laminar flow of filtered/sterilized air over the vials during the filling and/or transporting thereof. The sterile filling assembly may be adapted to fill vials, syringes, or other dispensers for containing medicaments, such as vaccines or pharmaceutical products. However, as may be recognized by those skilled in the pertinent art based on the teachings herein, the sterile filling assembly equally may be used for filling any of numerous other substances, such as cosmetics and food products. The sterile filling assembly comprises an infeed unit 86 for holding the vials, syringes or other containers to be delivered into the enclosure 84 of the sterile filling assembly. In the illustrated example, the infeed unit 86 is in the form of a rotary table that holds a plurality of vials, syringes or other containers, and delivers the containers at a predetermined rate into the sterile filling assembly. As may be recognized by those skilled in the pertinent art based on the teachings herein, the infeed unit may take the form of any of numerous devices that are currently, or later become known for performing the functions of the infeed unit 86, such as any of numerous different types of vibratory feed drives, or "pick and place" robotic systems.

Prior to installing the vials or other containers on the infeed unit 86, the sealed containers (e.g., the empty vials with the cap and valve assemblies sealed thereto) are preferably sterilized, such as by exposing the containers to gamma radiation, in a manner known to those of ordinary skill in the pertinent art. In addition, the vial assemblies or other sealed, empty containers, may be enclosed, sterilized, and transported to the sterile filling assembly in accordance with the teachings of U.S. Pat. No. 5,816,772, entitled "Method of Transferring Articles, Transfer Pocket And Enclosure," and U.S. patent application Ser. No. 10/241,249, entitled "Transfer Port and Method for Transferring Sterile Items", each of which is assigned to the assignee of the present invention and is hereby expressly incorporated by reference as part of the present disclosure.

Once loaded into the sterile filling assembly, the vials or other containers may be sterilized again (or alternatively, sterilized for the first time) by transmitting radiation from a radiation source 88 onto the sealed, empty vials in order to further ensure absolute sterility of the requisite surfaces prior to filling. The radiation may take the form of any of numerous different types of radiation that are currently or later become known for performing this function, such as gamma, e-beam and/or laser radiation.

A conveyor 90 is coupled to the infeed unit 86 for receiving the vials delivered by the infeed unit and for transporting the vials at a predetermined rate through the sterile filling assembly. In the illustrated example, the conveyor 90 transports the containers in a single file relative to each other. The conveyor 90 may take the form of any of numerous different types of conveyers that are currently, or later become known, for performing the functions of the conveyor described herein. For example, the conveyor may take the form of a vibratory feed drive, or may take the form of an endless conveyor belt, or a plurality of star wheels, including, for example, a plurality of receptacles, such as cleats, for receiving or otherwise holding the vials at predetermined positions on the conveyor. The conveyor is drivingly connected to a motor or other suitable drive source (not shown), which is controlled by a computer or other control unit (not shown) to start, stop, control the speed, and otherwise coordinate operation of the conveyor with the other components of the sterile filling assembly.

The radiation source 88 may includes at least one e-beam source mounted within an e-beam housing 87 (not shown in FIG. 9) containing therein a filling station 77 including the filling members 72. The e-beam source 88 may be any of numerous different types of e-beam sources that are currently, or later become known, for performing the function of the e-beam source described herein. E-beam radiation is a form of ionizing energy that is generally characterized by its low penetration and high dose rates. The electrons alter various chemical and molecular bonds upon contact with an exposed product, including the reproductive cells of microorganisms, and therefore e-beam radiation is particularly suitable for sterilizing vials, syringes and other containers for medicaments or other sterile substances. As indicated by the arrows in FIG. 9A, the e-beam source 88 produces an electron beam 89 that is formed by a concentrated, highly charged stream of electrons generated by the acceleration and conversion of electricity. Preferably, the electron beam 89 is focused onto the surface of each container for engagement by the filling member 72 to open the valve and allow the container to be filled with a medicament or other substance. For example, in the case of vials, such as the vials including valve assemblies as described above, the electron beam 89 is focused onto the upper surface of the valve member 20 and hub 24 of the vial or cap assemblies prior to engagement by the filling member 72. In addition, reflective surfaces may be mounted on opposite sides of the conveyor relative to each other to reflect the e-beam, and/or the reflected and scattered electrons, onto the sides of the vial assemblies to sterilize these surfaces as well. Alternatively, or in combination with such reflective surfaces, more than one e-beam source may be employed, wherein each e-beam source is focused onto a respective surface or surface portion of the vials or other containers to ensure sterilization of each surface area of interest.

The e-beam housing is constructed in a manner known to those of ordinary skill in the pertinent art to define an e-beam chamber and means for preventing leakage of the electrons out of the chamber in accordance with applicable safety standards. The conveyor 90 may define an approximately U-shaped path within the e-beam chamber 87, wherein the first leg of the U defines an inlet section and the portion of the chamber onto which the e-beam is directed. Preferably, the current, scan width, position and energy of the e-beam 89, the speed of the conveyor 90, and/or the orientation and position of any reflective surfaces, are selected to achieve at least a 3 log reduction, and preferably about a 6 log reduction in bioburden testing on the exposed or upper surface of the valve member 20, i.e., the surface of the valve member engaged by the filling member 72, and on the surfaces of the filling member 72 that contact the vials. In addition, as an added measure of caution, one or more of the foregoing variables also are preferably selected to achieve at least a 3 log reduction on the sides of the vial and non-contact surfaces of the filling members. These specific levels of sterility are only exemplary, however, and the sterility levels may be set as desired or otherwise required to validate a particular product under, for example, United States FDA or applicable European standards, such as the applicable Sterility Assurance Levels ("SAL").

The sterile filling assembly 84 also preferably includes means for visually inspecting the filling station 77. This means may take the form of a beta-barrier window (i.e., a window that blocks any e-beam radiation but permits visual inspection therethrough), and/or a CCD, video or other camera mounted within the housing for transmitting to an external monitor images of the filling station. As may be recognized by those skilled in the pertinent art based on the teachings herein, these particular devices are only exemplary, and any of numerous other devices that are currently known, or later become known, for performing the function of permitting visual inspection equally may be employed.

The filling station 77 is located on the opposite leg, or outlet side of the U-shaped conveyor path within the e-beam chamber. The filling station 77 may include a plurality of filling members 72 mounted over the conveyor 90, wherein each filling member is drivingly mounted over the conveyor in the same manner as described above. Accordingly, each filling member 72 is movable into and out of engagement with the valve members 20 of the vials or other containers received within the filling station to fill the vials or other containers with a medicament or other substance to be contained therein, and to then withdraw the filling member upon filling the vials or other containers. The filling station may include a bank of six filling members 72 mounted in line with each other and overlying the conveyor 90 to allow the simultaneous in-line filling of six vials or other containers. The filling members 72 may be mounted to a common drive unit 75 (as shown in FIG. 9), or each filling member may be individually actuatable into and out of engagement with the valve members of the vials or other containers. As may be recognized by those of ordinary skill in the pertinent art based on the teachings herein, the filling station may include any desired number of filling members, or may be mounted or driven in any of numerous different ways that are currently known, or later become known, for performing the functions of the filling station described herein. Similarly, the sterile filling assembly may include a plurality of filling stations mounted within the same e-beam chamber, or a plurality of e-beam and filling assemblies, in order to increase or otherwise adjust the overall throughput of the sterile filling assembly. Preferably, the e-beam housing 87 defines a port or other removable passageway (not shown) to allow access to and/or repair and replacement of the filling station 77.

As described above, the e-beam and filling station is configured so that the filling members 72 are mounted within the e-beam chamber 87. As a result, the free electrons within the e-beam chamber will impinge upon the filling members. This, in combination with operation of the e-beam 79 that sterilizes the air throughout the e-beam chamber 87, functions to sterilize the filling members and/or maintain the sterility of the filling members throughout the filling process. Accordingly, since the containers or other vials are filled within the e-beam chamber 87, there is virtually no risk that the vials will become contaminated between e-beam sterilization and filling. If desired, the air within the e-beam chamber may be ionized to promote multiplication of the free electrons and further enhance the sterility of the filling station 84. Furthermore, this feature obviates any need for an isolator, as found in many prior art sterile filling machines.

The e-beam source 88 and other applicable components of the e-beam chamber, conveyor systems, and filling assembly may be the same or similar to that disclosed in the following co-pending patent applications which are assigned to the Assignee of the present invention and hereby incorporated by reference as part of the present disclosure: U.S. application Ser. No. 10/600,525 (U.S. Pat. No. 6,929,040), entitled "Sterile Filling Machine Having Needle Filling Station Within E-Beam Chamber"; U.S. provisional application Ser. No. 60/518,267, filed Nov. 7, 2003, entitled "Needle Filling and Laser Sealing Station"; and U.S. provisional application Ser. No. 60/518,685, filed Nov. 10, 2003, entitled "Needle Filling and Laser Sealing Station".

As shown in FIG. 9, the sterile filling assembly includes a laminar flow source 92 of a type known to those of ordinary skill in the pertinent art for providing a laminar flow of filtered/sterilized air over the vials or other containers during the filling thereof. The laminar flow source 92 is particularly advantageous in those applications where the vial assemblies are not filled in an e-beam chamber as illustrated in FIG. 32.

As shown in FIG. 9A, the sterile filling assembly may include one or more additional stations 79 located downstream of the filling station 77. The additional stations 79 may include a lyophilization station, as described further below, a vision system of a type known to those of ordinary skill in the pertinent art for inspecting each valve seal, a level detection system for detecting the level of fluid or other substance within each vial or other container to ensure that it is filled to the correct level, and a labeling station. In addition, as shown in FIG. 9A, the sterile filling assembly may include a rejection unit 81 for pulling off of the conveyer any vials or other containers that are defective as detected, for example, by the level detection inspection, or due to mislabeling or defective labeling. Then, the acceptable vials or other containers are removed by a discharge unit 83 for discharging the vials or other containers into a collection unit 85 for packing and shipping. The rejection and discharge units may take the forms of star wheels, pick and place robots, or any of numerous other devices that are currently or later become known for performing the functions of these units described herein.

To significant advantage true sterile filling is enabled, not only aseptic filling. Yet another advantage is that the medicament or other substance is filled after subjecting the containers to gamma and direct e-beam radiation, thus preventing the radiation from degrading the medicament or other substance to be contained within the container.

In order to withdraw the substance from the vial, and as shown in FIG. 10, the open end 98 of a syringe 94 is threadedly connected to the mounting surface 28 of the cap assembly 14. A typical syringe 94 includes a threaded female connector 96 for attaching thereto a needle (not shown). One such connector 96 is sold under the trademark Leur Lock™. Accordingly, the mounted surface 28 of the vial is threadedly received within the female connector 96 of the syringe to releasably connect the vial to the syringe. This, in turn, causes the open end 98 of the syringe to axially engage and depress the nubs 56 formed on the valve member 20 to, in turn, move the valve member from the closed position to the open position, as shown in FIG. 10. Then, with the valve member 20 located in the open position, a plunger 100 on the syringe 94 is drawn outwardly to create a vacuum and, in turn, draw the substance 78 within the chamber 22 of the vial through the valve opening 74 and into the chamber of the syringe 94. Upon removing the desired volume of substance 78 from the chamber 22 of the vial, the syringe 94 is then disconnected from the vial by rotating the vial and/or syringe relative to the other. Upon removing the vial 10 from the syringe 94, the spring 58 axially moves the valve member 20 into the closed position and hermetically seals the remaining substance 78 located within the chamber 22 of the vial.

As may be recognized by those of ordinary skill in the pertinent art based on the teachings herein, the connector parts of the vial and/or syringe may take any of numerous different configurations that are currently or later become known for performing the functions of these parts as described herein. For example, the vial or other container or dispenser could form a male connector and the syringe could form a female connector. Alternatively, a different type of threaded connector, or a connector other than a threaded connector, equally could be used.

To significant advantage, the vial or other container or dispenser may hold multiple doses of substances and store the substance remaining within the vial in a hermetically sealed, sterile condition between doses. Accordingly, the substance shown may be a non-preserved vaccine or other injectable product. Because the vial maintains the substance in a sterile, hermetically sealed condition, from the first to the last dose, the use of preservatives may be avoided.

Figure 11:
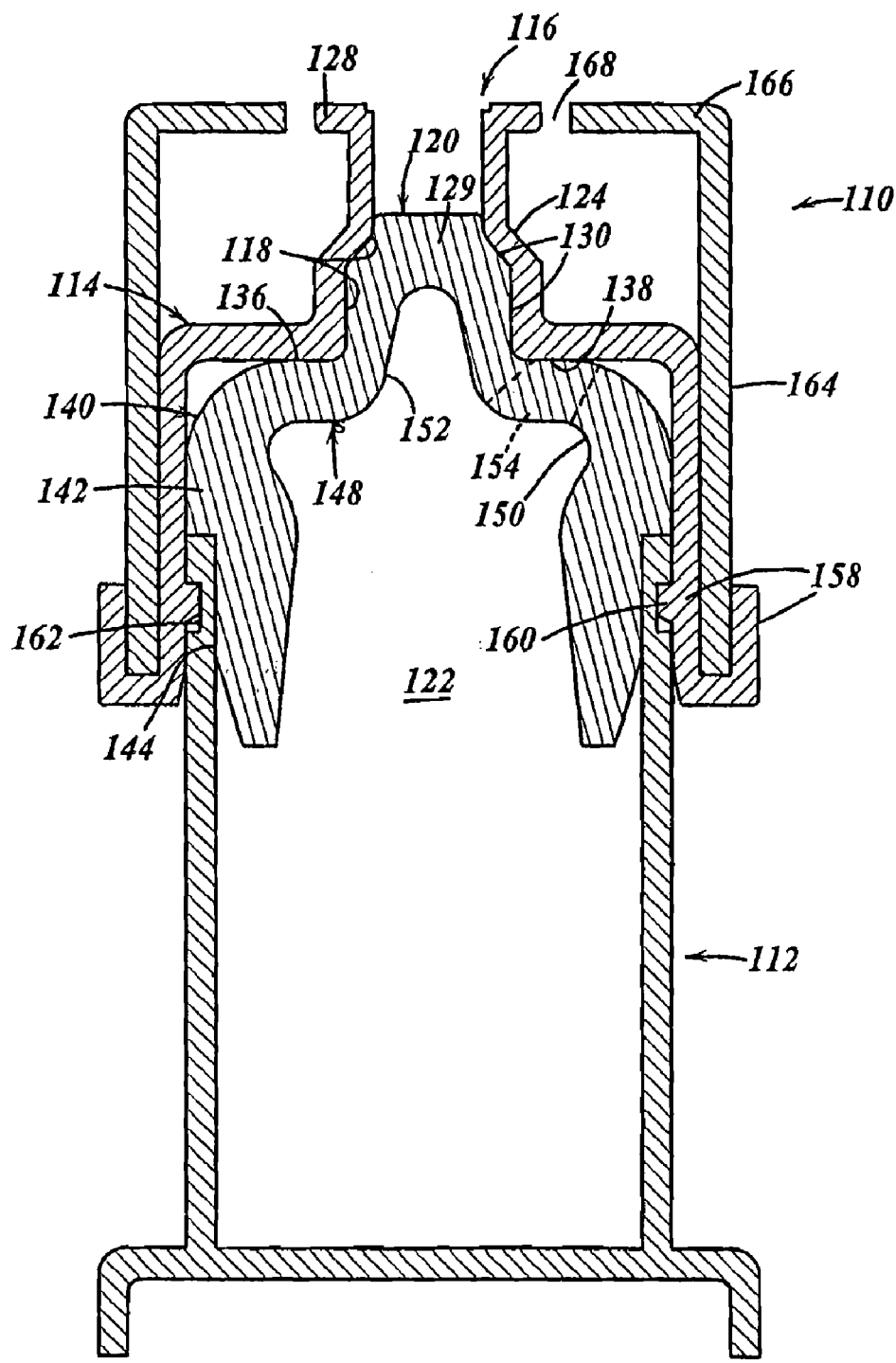
FIG. 11 is a cross-sectional view of another vial assembly including a different shaped spring than the vial assembly of FIG. 1.
Figure 12:
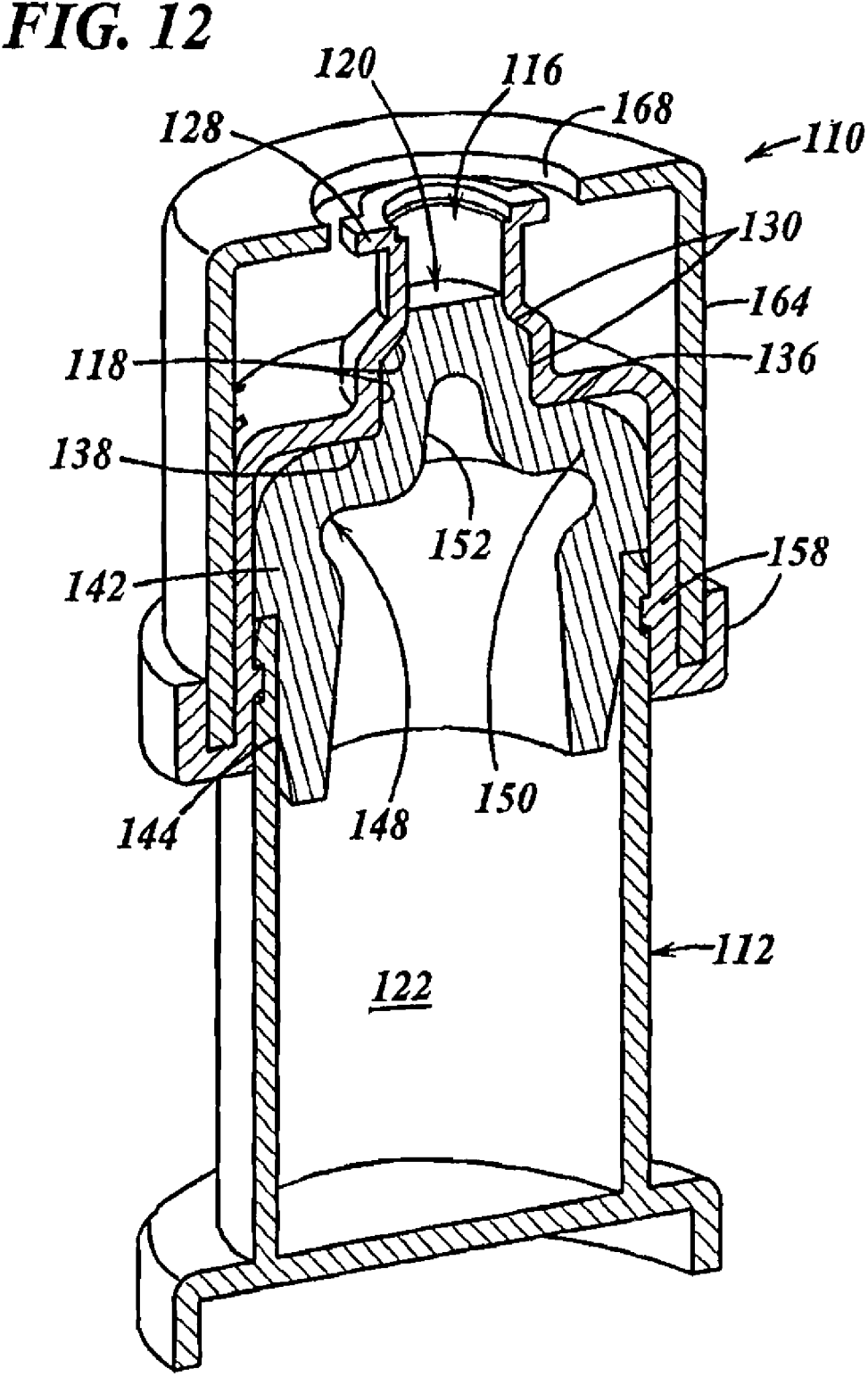
FIG. 12 is a perspective, cross-sectional view of the vial assembly of FIG. 11.
Figure 13:
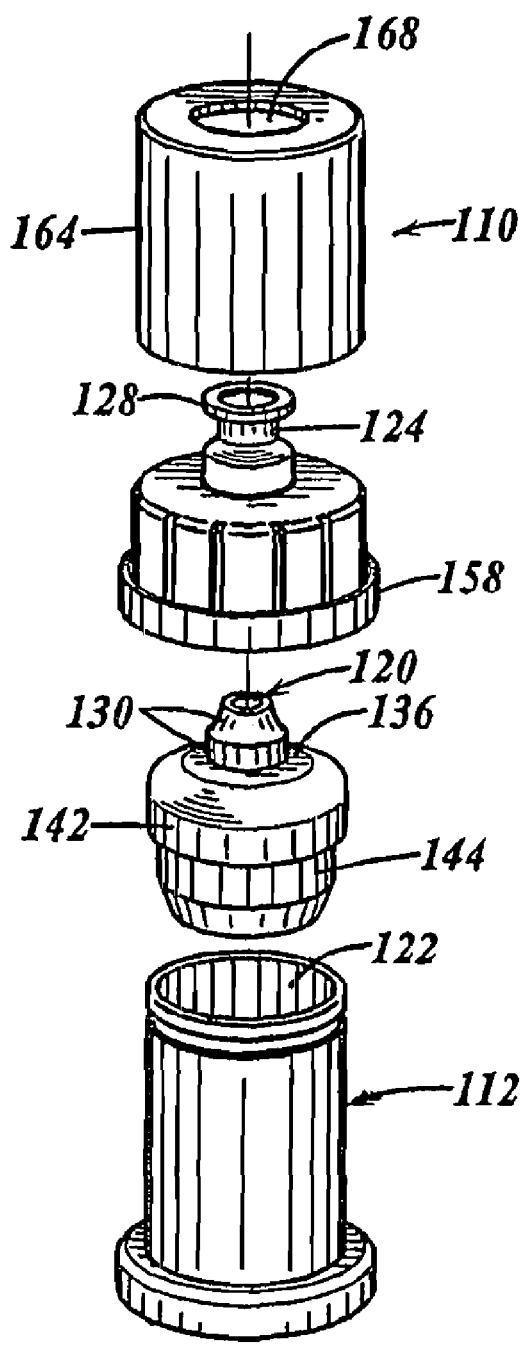
FIG. 13 is an exploded, perspective view of the vial assembly of FIG. 11.

In FIGS. 11-13, another vial assembly is indicated generally by the reference numeral 110. The vial assembly 110 is similar to the vial assembly 10 described above, and therefore like reference numeral preceded by the numeral "1", or preceded by the numeral "2" instead of the numeral "1", are used to indicate like elements. The primary difference of the vial assembly 110 in comparison to the vial assembly 10 is in the shape of the valve member 120 and the manner in which the valve member is seated within, and sealingly engages the hub 124 of the cap assembly 114. As can be seen, the integral spring 148 defines an annular, curvilinear shaped portion 150 defining a different dome shape than the corresponding dome-shaped portion 50 described above. In addition, the upper or exposed surface of the valve member 120 is recessed within the hub 124, and the sealing surfaces 118 and 138 of the valve seat, and the corresponding sealing surfaces 130 and 136, respectively, of the valve member, are shaped differently than the corresponding features described above. The vial 110 is filled with a medicament or other substance in the same manner as the vial 10 described above in connection with FIGS. 9 and 9A.

Figure 14:
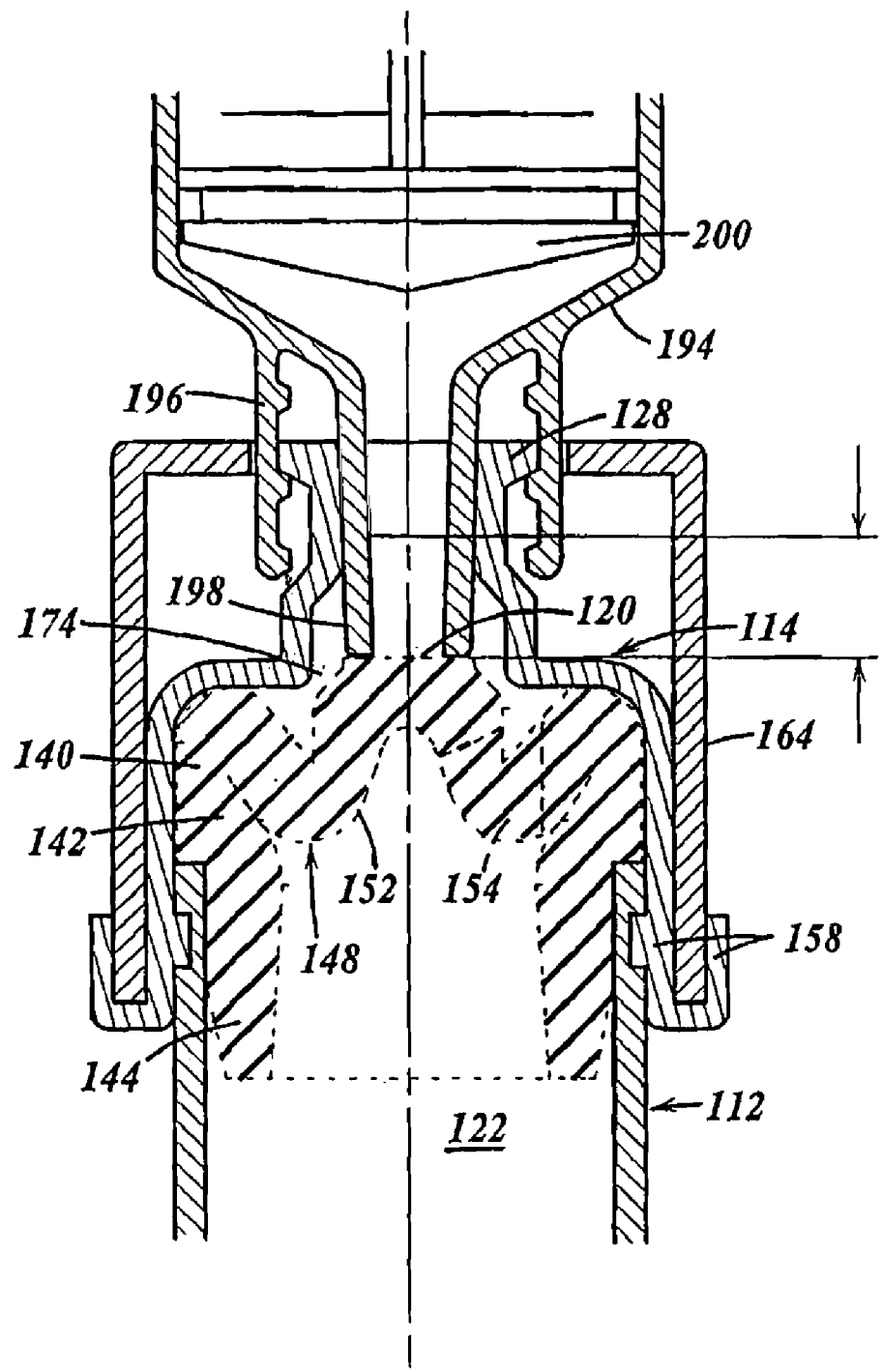
FIG. 14 is a partial, cross-sectional view of the vial assembly of FIG. 11 showing a syringe connected thereto for withdrawing substance from the vial chamber, through the valve assembly, and into the syringe.

FIG. 14 shows the open end 198 of a syringe 194 threadedly connected to the mounting surface 128 of the cap assembly 114 via threaded female connector 196 to releasably connect the vial to the syringe. This, in turn, causes the open end 198 of the syringe to axially engage and depress the valve member 120 to, in turn, move the valve member from the closed to the open position. Then, with the valve member 120 located in the open position, a plunger 200 on the syringe 194 is drawn outwardly to create a vacuum and, in turn, draw the substance (not shown) within the chamber 122 of the vial through the valve opening 174 and into chamber of the syringe 194. Upon removing the desired volume of substance from the chamber 122 of the vial, the syringe 194 is then disconnected from the vial by rotating the vial and/or syringe relative to the other. Upon removing the vial 110 from the syringe 194, the valve member 120 returns to the closed position and hermetically seals the remaining substance located within the chamber 122 of the vial.

In FIGS. 15 and 16, another vial assembly is indicated generally by the reference numeral 310. The vial assembly 310 is similar to the vial assembly 10 described above, and therefore like reference numeral preceded by the numeral "3", instead of the numeral "1", are used to indicate like elements. A principal difference of the vial assembly 310 in comparison to the vial assembly 10 is in the construction of the valve assembly. As can be seen, the valve assembly 316 includes a flexible valve member 320 that is formed separate from the base 340. The cap assembly 314 includes a downwardly-extending flange 324 located on the opposite side of the cap relative to the hub 324 and forming therein a cylindrical chamber for receiving the base of the valve member 320. The base 340 defines a flange 342 forming a hermetic seal between the cap assembly and body (not shown) in the same manner as described above; however, the base 340 further defines a bellows-like spring portion 350 that contacts the inner end of the valve member 320. As shown in FIG. 15, the spring portion 350 normally biases the valve member 320 into the closed position, and as shown in FIG. 16, the spring portion 350 is adapted to extend axially inwardly in response to a force applied to the exposed end of the valve member 320, as indicated by the arrow in FIG. 16, such as the force applied by a filling member or syringe, as described above, in order to depress or move the valve member inwardly and, in turn, open the valve at 374.

The valve member 320 further includes a peripheral sealing surface 330 that sealingly engages the valve seat 318, and a sealing member 336 located on the interior side of the valve seat 318 and defining a peripheral surface that sealingly engages the corresponding surface 338 formed on the hub 324 to further effect a fluid-tight seal in the closed position. The valve member 320 further defines an axially extending passageway 337 formed in the base portion thereof and coupled in fluid communication between the valve opening 374 (FIG. 16) and the flow aperture 354 extending through the spring portion 350 to allow fluid flow through the valve, as indicated by the arrows in FIG. 16. The vial assembly 310 may be filled in the sterile filling assembly, and the fluid may be withdrawn from the vial assembly 310 and into a syringe, in the same manner as described above in connection with the vial assembly 10.

Figure 17:
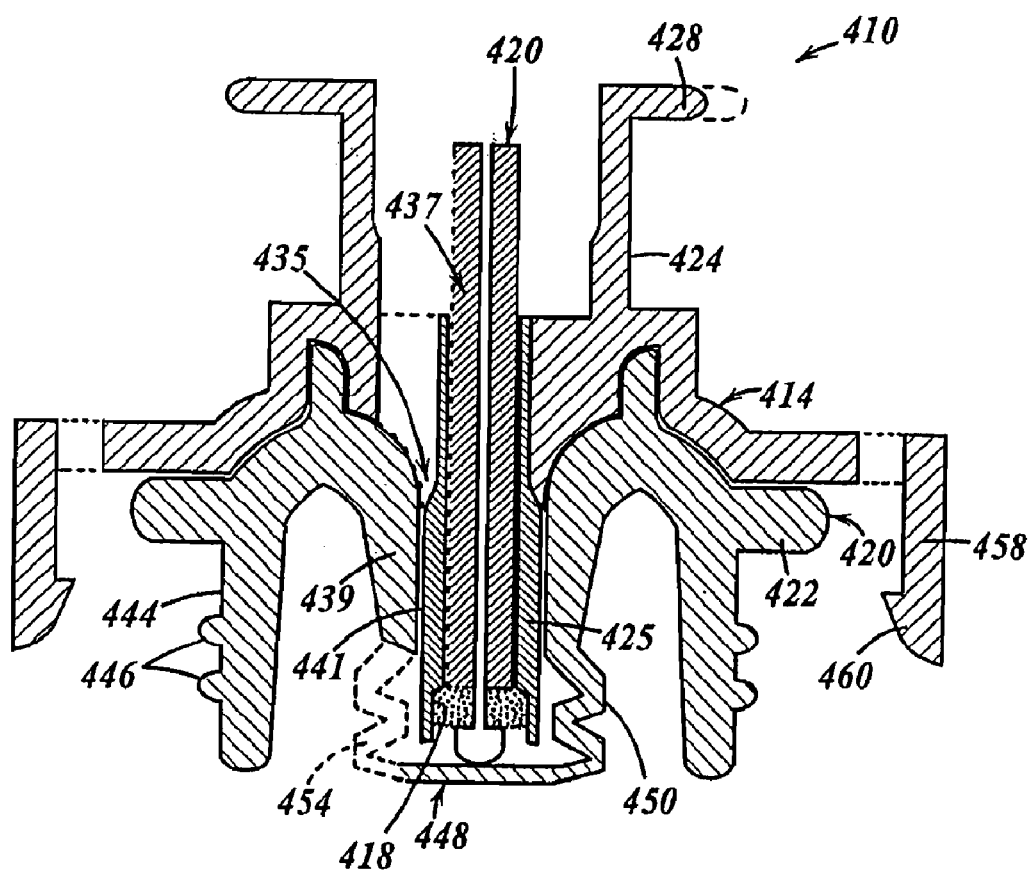
FIG. 17 is a partial, cross-sectional, somewhat schematic view of another vial assembly wherein the valve assembly includes a rigid valve member and bellows-shaped spring.
Figure 21:
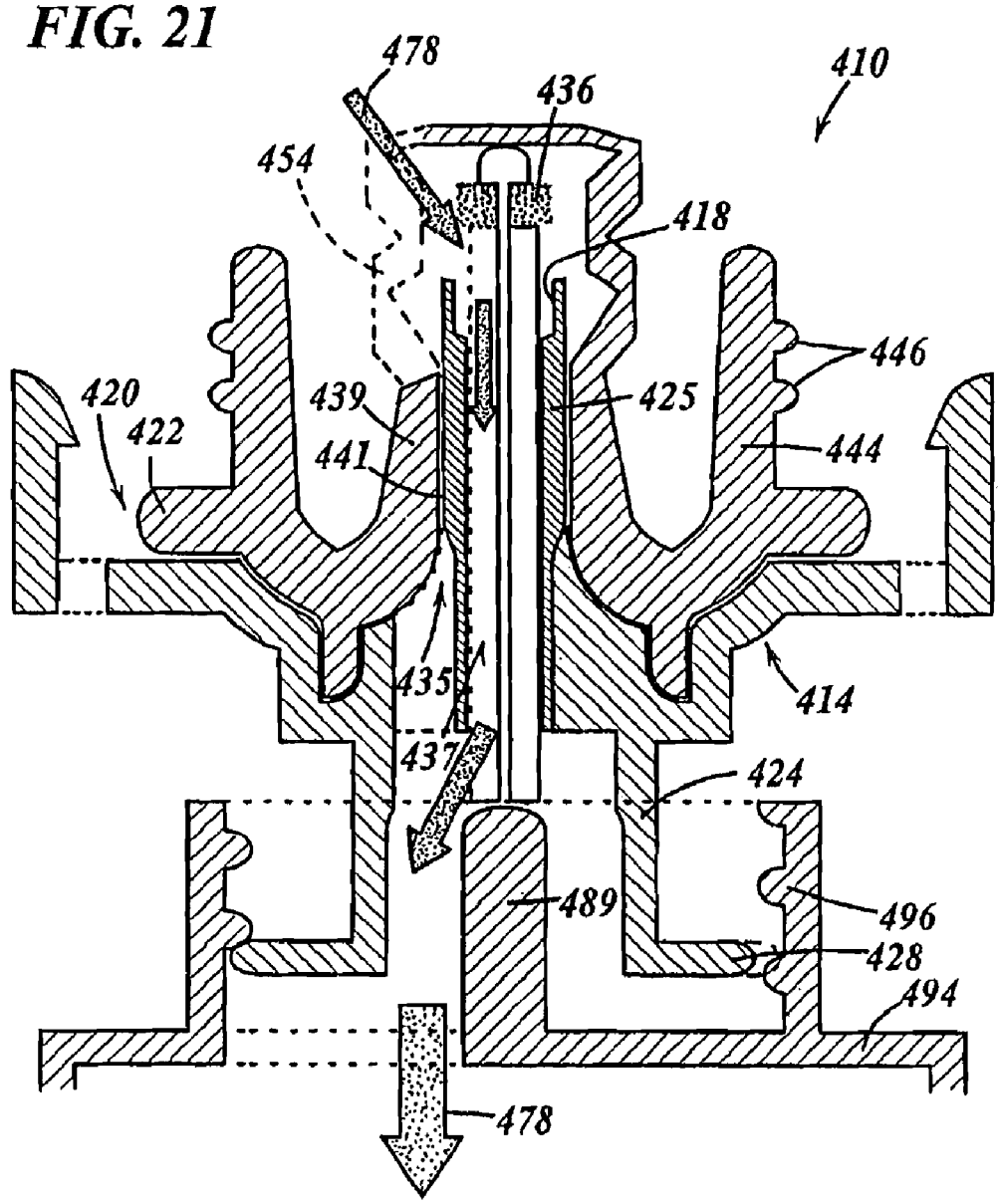
FIG. 21 is a partial, cross-sectional, somewhat schematic view of the vial assembly of FIG. 17 showing the flow of substance from the vial assembly into the syringe.
Figure 22:
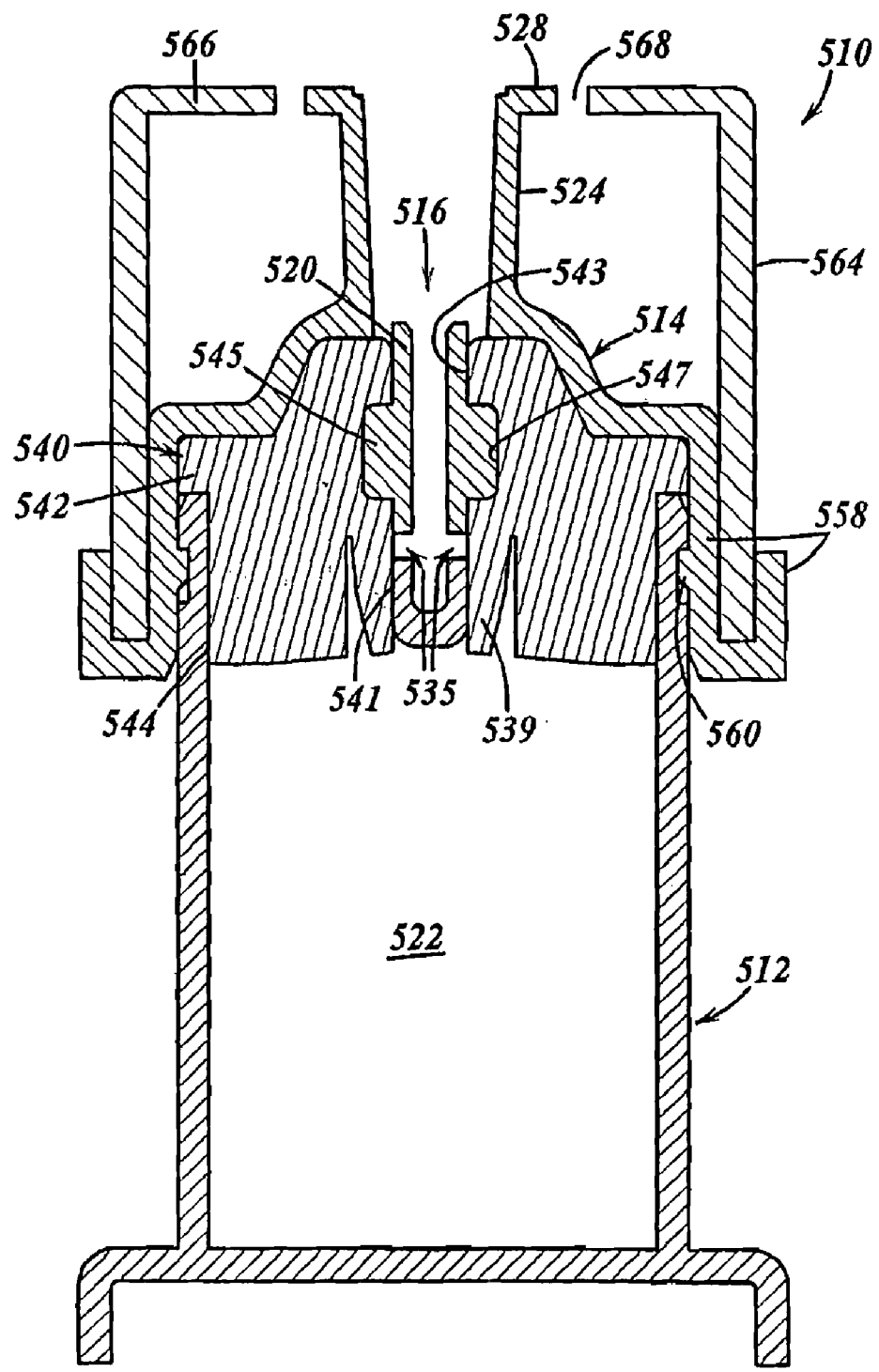
FIG. 22 is a cross-sectional view of another vial assembly that includes a valve assembly for filling the vial.
Figure 23:
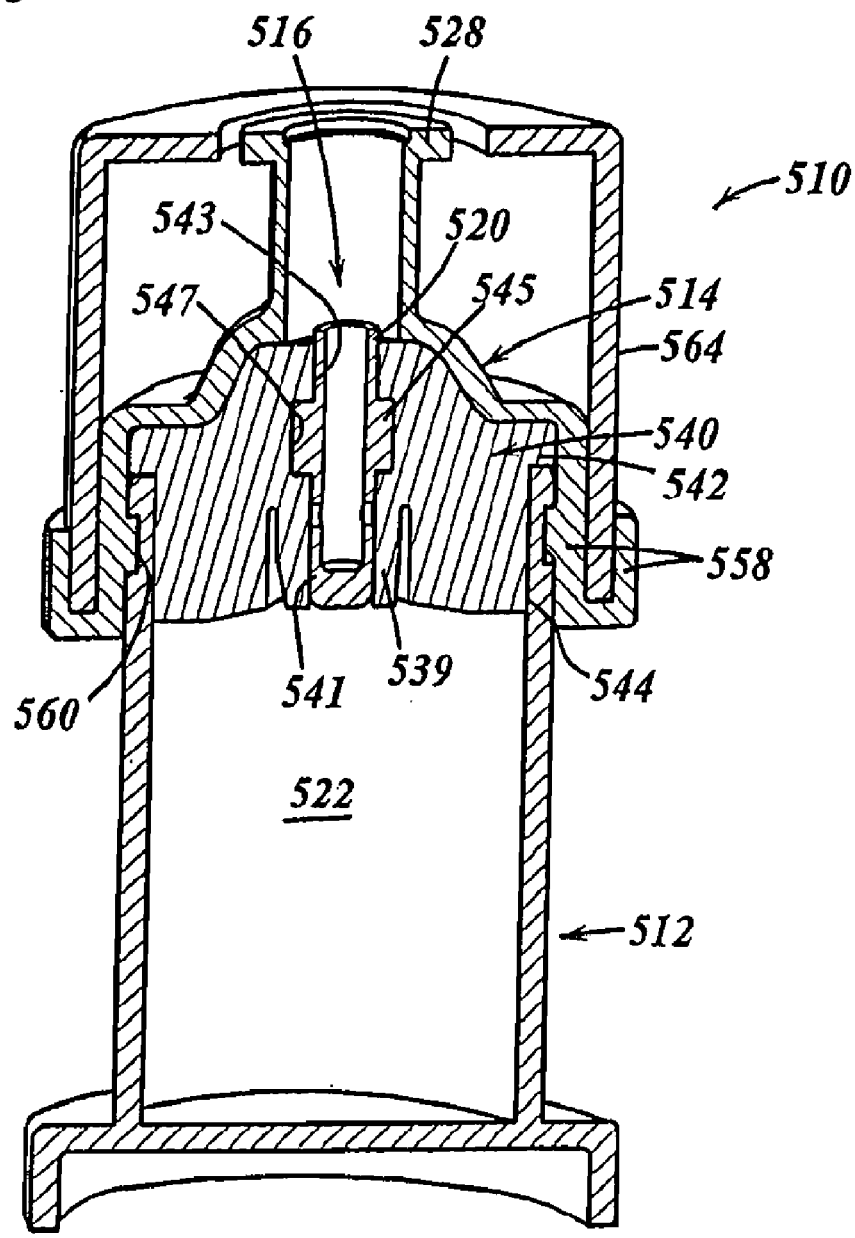
FIG. 23 is a perspective, cross-sectional view of the vial assembly of FIG. 22.
Figure 24:
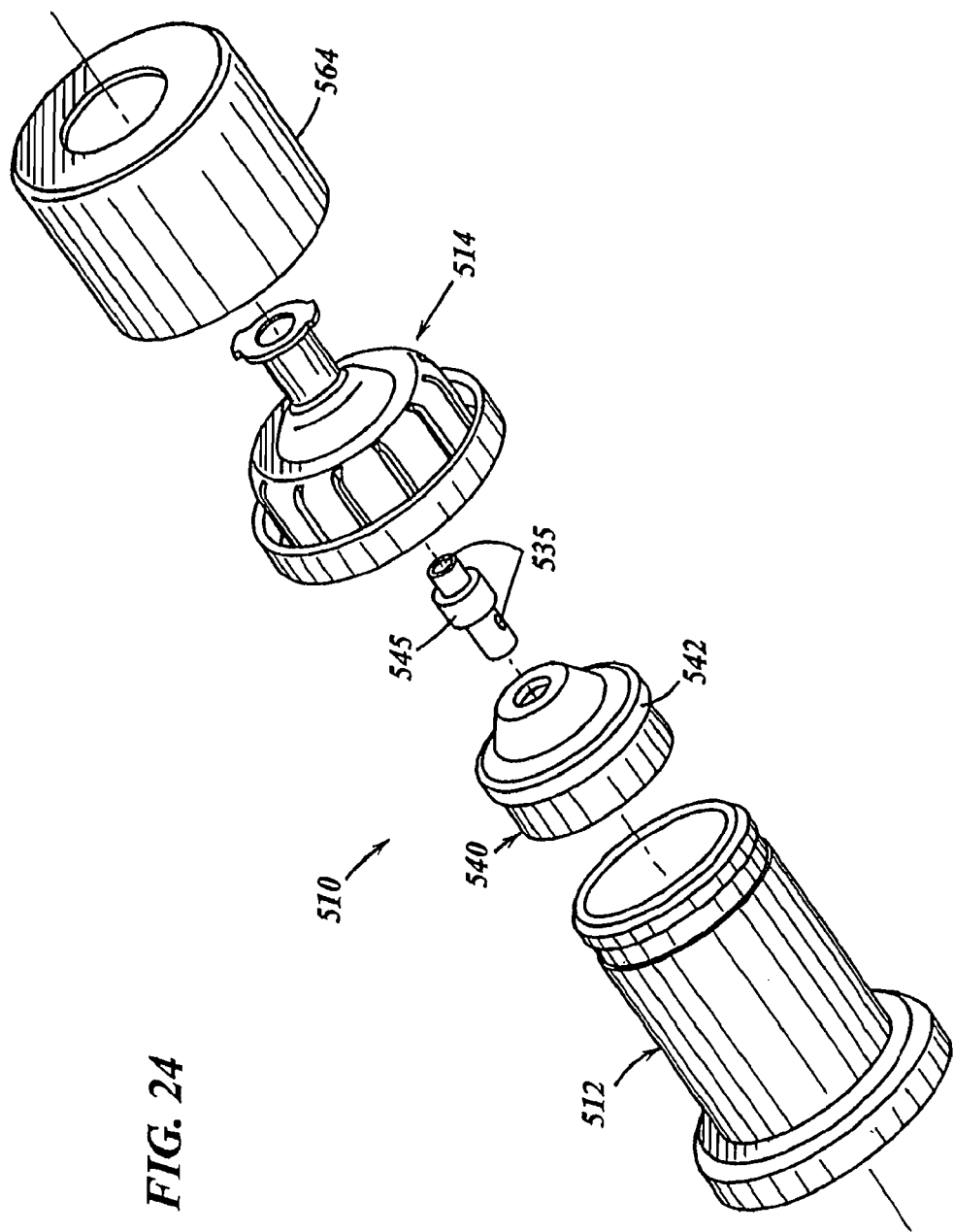
FIG. 24 is an exploded, perspective view of the vial assembly of FIG. 22.

In FIGS. 17-21, another vial assembly is indicated generally by the reference numeral 410. The vial assembly 410 is similar to the vial assembly 310 described above, and therefore like reference numerals preceded by the numeral "4", instead of the numeral "3", are used to indicate like elements. A principal difference of the vial assembly 410 in comparison to the vial assembly 310 is in the construction of the valve assembly. The valve assembly 410 defines a first flow path 435 for filling the vial assembly 410 with a substance, and a second flow path 437 for withdrawing the substance from the interior chamber of the vial assembly and into a syringe. As shown in FIG. 17, the base 420 defines an annular, axially-extending valve portion 439 and the flange 425 of the cap 414 defines a corresponding axially-extending valve seat 441. As further shown in FIG. 17, the wall thickness of the valve portion 439 decreases in a direction moving axially from the base of the valve portion formed adjacent to the flange 422 toward the bellows or spring portion 450. In the normally-closed position, the valve portion 439 sealingly engages the valve seat 441 to form a fluid-tight seal. The base 420 is preferably made of an elastomeric material, as described above in connection with the valve member 20. The valve portion 439 forms an interference fit with the valve seat 441 to further effect a fluid-tight seal. As shown in FIG. 18, the vial assembly 410 is filled by introducing substance 478 from a filling member (not shown) at sufficient pressure into the valve opening 435 to cause the valve member 439 to flex outwardly and away from the valve seat 441 to thereby open the valve and allow the passage of substance therethrough and into the vial chamber 422.

In order to withdraw the substance from the vial chamber 422, the valve member 420 is relatively rigid and defines a fluid passageway 437 for allowing the flow of substance therethrough. As indicated in FIGS. 19 and 20, the threaded connector 496 of a syringe 494 threadedly engages the flange 428 of the hub 424 to depress the valve member 420 with the end portion 498 of the syringe. This, in turn, causes the sealing member 436 to move axially inwardly and away from the valve seat 418 to thereby open the valve and allow the flow of substance therethrough. As indicated by the arrows in FIG. 21, the substance is permitted to flow from the interior chamber 422 of the vial, through the axially-extended opening 454 in the bellows 450, through the flow path 437 of the valve, and into the interior chamber of the syringe. Upon releasing the syringe from the vial, the bellows 350 biases the valve member 420 back into its normally closed position to form a fluid-tight seal and thereby retain the remaining substance in the vial for later use.

Figure 25:
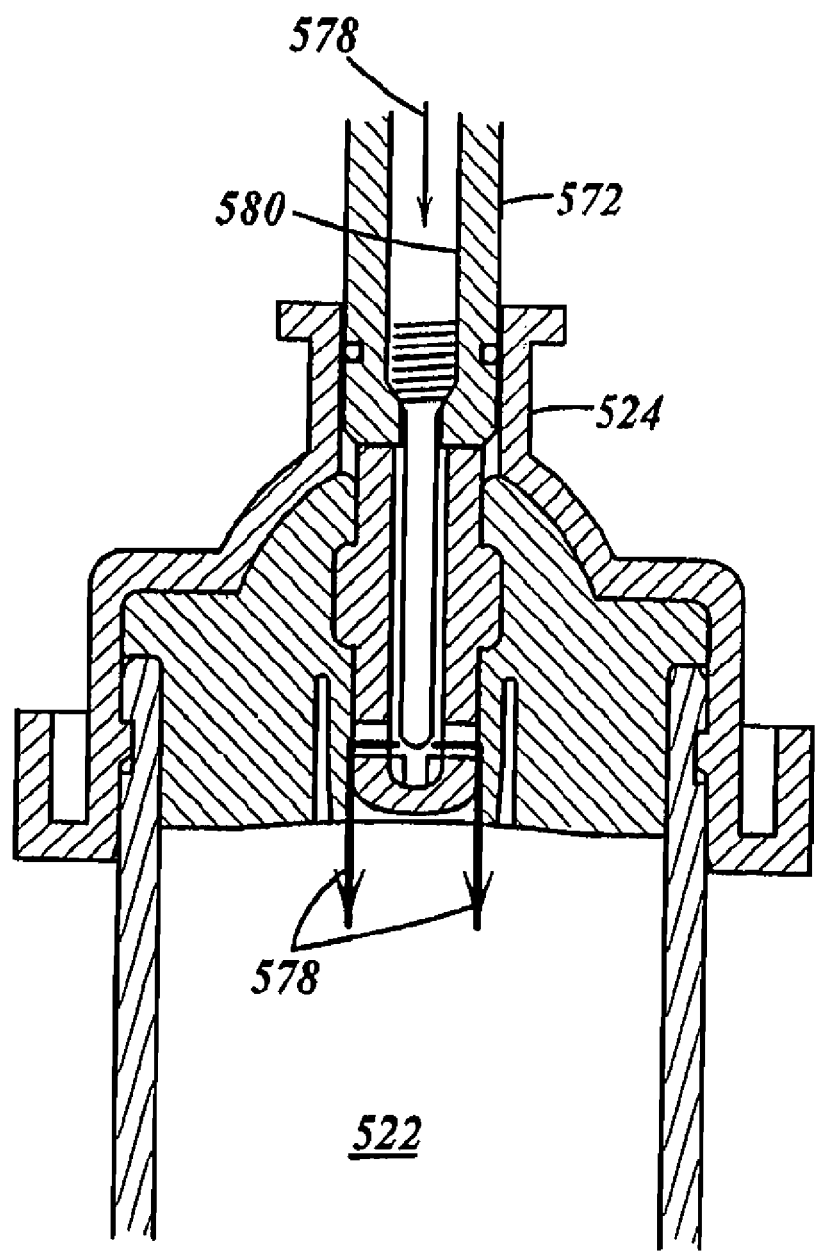
FIG. 25 is a partial, cross-sectional view of the vial assembly of FIG. 22 showing the filling thereof.

In FIGS. 22-26, another vial assembly is indicated generally by the reference numeral 510. The vial assembly 510 is similar to the vial assembly 410 described above, and therefore like reference numeral preceded by the numeral "5", instead of the numeral "4", are used to indicate like elements. A principal difference of the vial assembly 510 in comparison to the vial assembly 410 is in the construction of the valve assembly. The rigid valve member 520 defines a fluid conduit 535 extending therethrough and coupled in fluid communication with an inlet valve assembly including a rigid valve seat 541 formed by an outer surface of the valve member 520 and a flexible valve member 539 extending about the periphery of the rigid valve seat. As further shown in FIG. 22, the wall thickness of the valve portion 539 decreases in a direction moving axially from the base of the valve portion toward the interior chamber 522 of the vial. In the normally-closed position, the valve portion 539 sealingly engages the valve seat 541 to form a fluid-tight seal therebetween. The base 540 is preferably made of an elastomeric material, as described above in connection with the valve member 20. The valve portion 539 forms an interference fit with the valve seat 541 to further effect a fluid-tight seal. As shown in FIG. 25, the vial assembly 510 is filled by inserting a filling member 572 into the open end of the hub 524. The filling member 572 introduces substance 578 at sufficient pressure into the valve member 520 and valve openings 535 thereof to cause the valve member 539 to flex outwardly and away from the valve seat 541 and, in turn, open the valve to allow the passage of substance therethrough and into the vial chamber 522. The valve portion 539 and the valve seat 541 may take any of numerous different shapes and/or configurations that are currently known, or that later become known, such as any of the shapes and/or configurations disclosed in the following co-pending patent applications that are assigned to the Assignee of the present invention and are hereby expressly incorporated by reference as part of the present disclosure: U.S. application Ser. No. 10/640,500 (U.S. Pat. No. 6,892,906), filed Aug. 13, 2003, entitled "Container and Valve Assembly for Storing and Dispensing Substances"; U.S. provisional application Ser. No. 60/528,429, filed Dec. 10, 2003, entitled "Valve Assembly and Tube Kit for Storing and Dispensing Substances"; and U.S. provisional application Ser. No. 60/539,602, filed Jan. 27, 2004, entitled "Tubular Container and One-Way Valve Assembly for Storing and Dispensing Substances".

Figure 26:
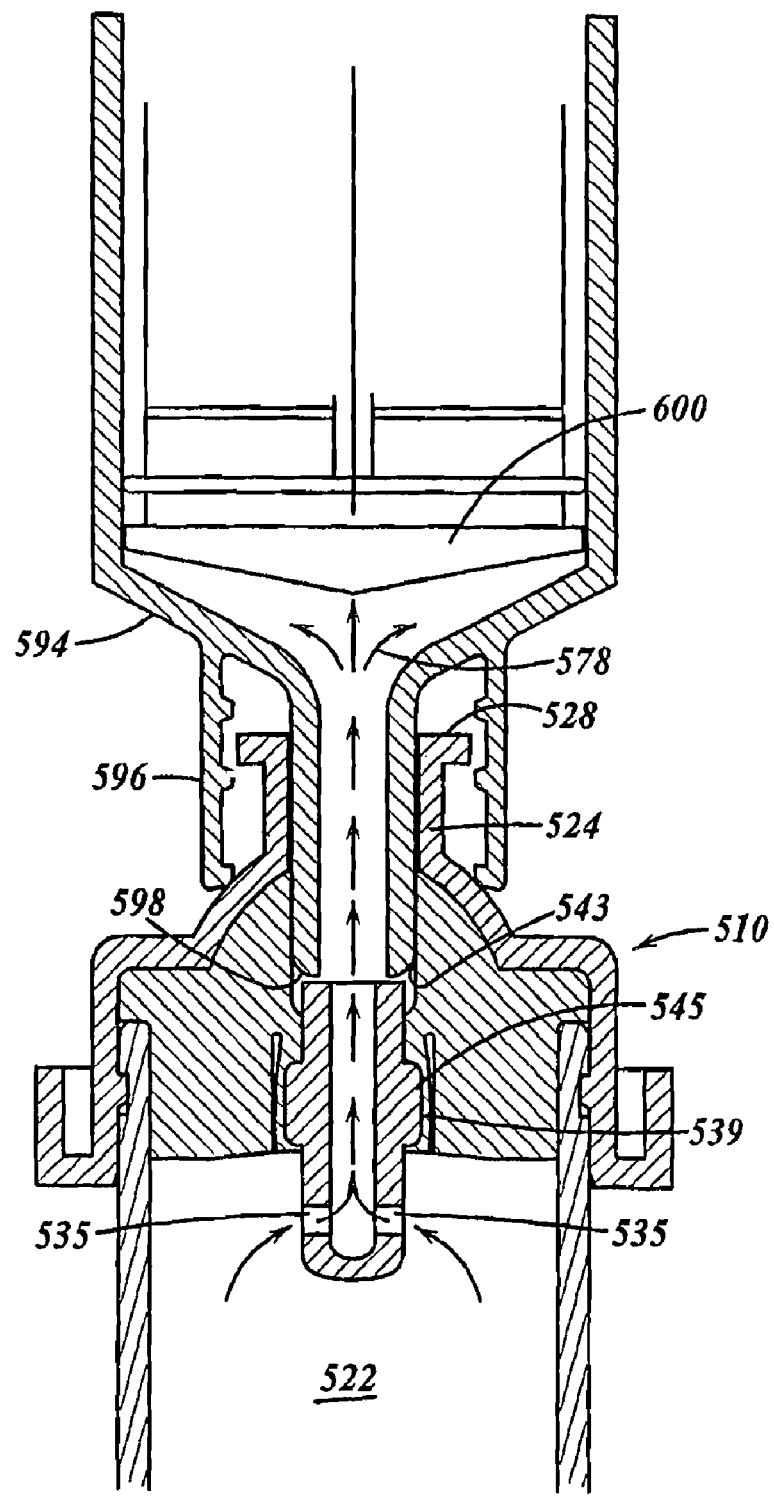
FIG. 26 is a partial, cross-sectional view of the vial assembly of FIG. 22 showing the withdrawal of substance therefrom and into a syringe.

As shown in FIGS. 22-26, the base 540 defines an axially-extending aperture 543 therethrough for receiving the rigid valve member 520, and the valve member defines a peripheral flange 545 that is received within a corresponding recess 547 formed within the base 540 to releasably secure the valve member within the base. As shown in FIG. 26, in order to withdraw substance 578 from the vial chamber 522 into a syringe 594, the connector 596 on the syringe is secured to the hub 524 of the vial assembly 510, such as by threadedly engaging a female connector 596 of the syringe to the flange 528 on the vial hub 524. This, in turn, causes the tip 598 of the syringe to engage the end surface of the valve member 520 and depress the valve member axially inwardly through the aperture 543. As shown in FIG. 26, when the syringe 594 is fully connected to the vial, the rigid valve member 520 is moved axially through the aperture 543 a distance sufficient to space the apertures beyond and out of engagement with the flexible valve member 539 and into fluid communication with the interior chamber 522 of the vial. In this position, the plunger 600 of the syringe may be withdrawn to, in turn, draw substance within the chamber 522 through the apertures 535, through the valve member 520, and into the interior of the syringe. The syringe is then disconnected from the vial and a needle (not shown) is attached to the connector 596 of the syringe for injection into a patient.

Figure 27:
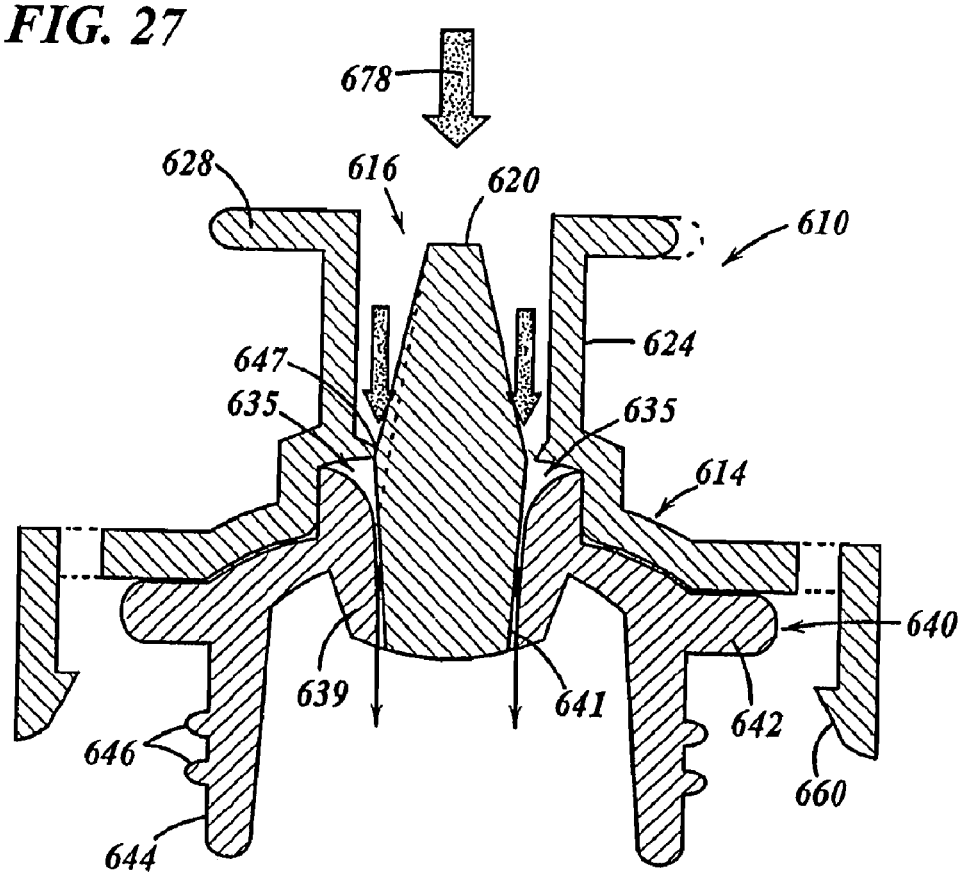
FIG. 27 is a partial, cross-sectional, somewhat schematic view of another vial assembly including a frangible valve member.

In FIGS. 27-30, another vial assembly is indicated generally by the reference numeral 610. The vial assembly 610 is similar to the vial assembly 510 described above, and therefore like reference numeral preceded by the numeral "6", instead of the numeral "5", are used to indicate like elements. A principal difference of the vial assembly 610 in comparison to the vial assembly 510 is in the construction of the valve assembly. The vial assembly 610 defines a fluid flow path 635 into the valve assembly 616 for filling the vial assembly 610 with a substance 678. As shown in FIG. 27, the base 640 defines an annular, axially-extending valve portion 639 and the rigid valve member 620 defines a corresponding axially-extending valve seat 641. As further shown in FIG. 27, the wall thickness of the valve portion 639 decreases in a direction moving axially from the exterior side of the valve portion that engages the cap 614 toward the interior chamber 622 of the vial assembly. In the normally-closed position, the valve portion 639 sealingly engages the valve seat 641 to form a fluid-tight seal. The base 640 is preferably made of an elastomeric material, as described above in connection with the valve member 20. The valve portion 639 forms an interference fit with the valve seat 641 to further effect a fluid-tight seal. As shown in FIG. 27, the vial assembly 610 is filled by introducing substance 578 from a filling member (not shown) at sufficient pressure into the valve opening 635 to cause the valve member 639 to flex outwardly and away from the valve seat 641 and thereby open the valve and allow the passage of substance therethrough and into the vial chamber 622.

Figures 28, 29:
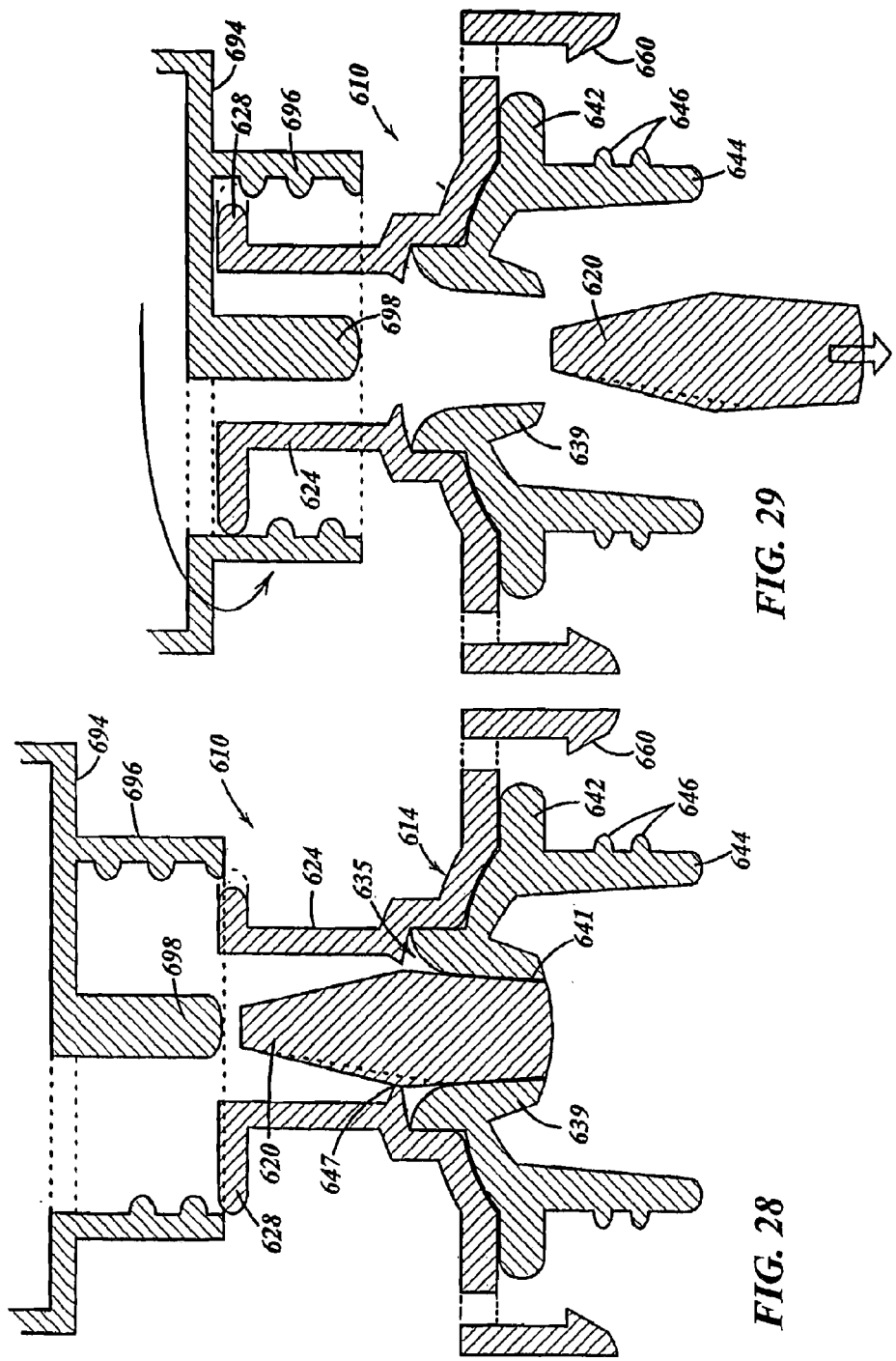
FIG. 28 is a partial, cross-sectional, somewhat schematic view of the vial assembly of FIG. 27 showing the connection of a syringe thereto.
FIG. 29 is a partial, cross-sectional, somewhat schematic view of the vial assembly of FIG. 27 showing the further connection of the syringe thereto and the fracturing of the frangible connection.
Figure 30:
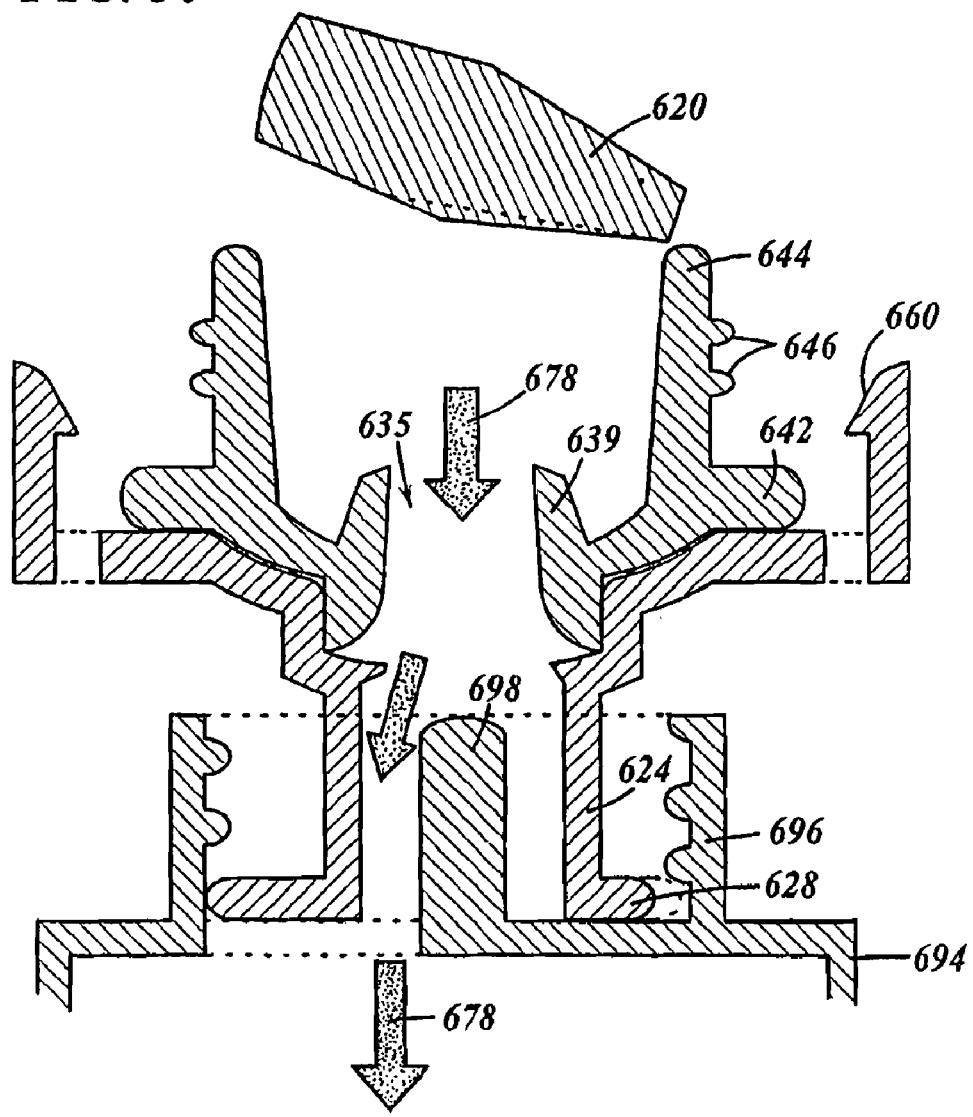
FIG. 30 is a partial, cross-sectional, somewhat schematic view of the vial assembly of FIG. 27 showing the withdrawal of substance from the vial chamber and into a syringe.

The rigid valve member 620 is releasably connected to the base of the hub 624 by a frangible connection 647. Thus, during filling of the vial, as described above, the rigid valve member 620 is fixedly secured to the cap 614 and functions as a valve seat for filling the vial and maintaining a fluid-tight seal with the valve portion 639 during storage of the vial. However, the frangible connection 647 is designed to permit the rigid valve member 620 to fracture when sufficient axial force is applied to the external end of the valve member 620 in order to allow removal of substance 678 from the vial. As shown in FIGS. 28-30, in order to withdraw substance 678 from the interior chamber 622 of the vial and into a syringe 694, the connector 696 of the syringe is secured to the flange 628 of the vial hub 624, such as by threadedly engaging the connector to the hub. As the syringe 694 is threadedly connected to the hub 624, the end surface 698 of the syringe engages the end surface of the rigid vial member 620 and applies an axial inward force thereto. When the syringe 694 is fully connected to the vial, the force applied to the valve member 620 is sufficient to break the frangible connection 647 and, in turn, release the valve member 620 from the cap 614 and into the chamber 622 of the vial. As indicated in FIG. 30, the plunger (not shown) of the syringe 694 is then actuated to draw substance 678 through the open end of the vial and into the syringe. The syringe is then disconnected from the vial and a needle (not shown) is attached to the connector 696 of the syringe for injection into a patient. The empty vial 610 may then be disposed of.

Figure 31:
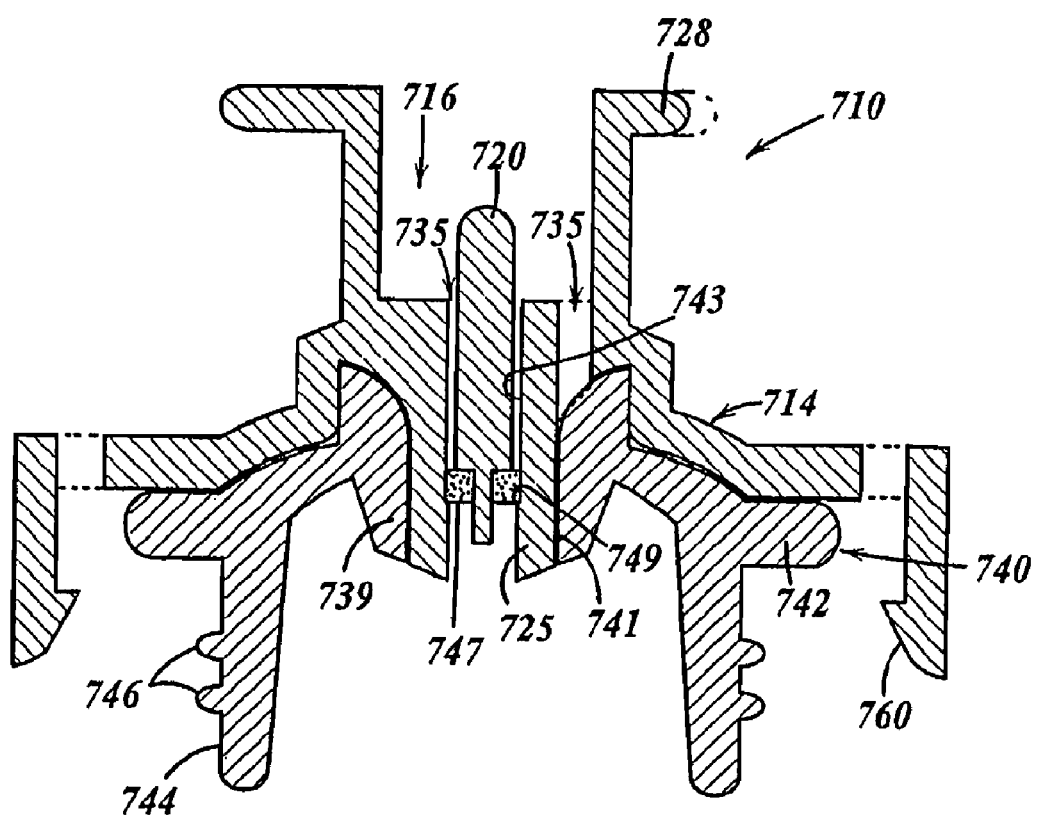
FIG. 31 is a partial, cross-sectional, somewhat schematic view of another embodiment of a vial assembly including another valve assembly.

In FIG. 31, another vial assembly is indicated generally by the reference numeral 710. The vial assembly 710 is similar to the vial assembly 610 described above, and therefore like reference numeral preceded by the numeral "7", instead of the numeral "6", are used to indicate like elements. A principal difference of the vial assembly 710 in comparison to the vial assembly 610 is in the construction of the valve assembly and frangible connection. As shown, the valve seat 741 is formed by an axially-extending flange 725 of the cap 714. The flange 725 defines an axially-extending aperture 743 therethrough. The rigid valve member 720 is received within the aperture 743, and a sealing/connection member 747 both releasably secures the valve member 720 within the aperture and forms a fluid tight seal therebetween. The rigid valve member 720 may take the form of any of numerous different gaskets or other sealing members that are currently known, or later become known for performing the function of the sealing/connection member as described herein. The flange 725 defines an annular lip 749 that acts as a stop to seat the sealing/connection member 747 upon inserting same with the rigid valve member into the aperture 743.

In order to fill the vial assembly 710, substance is introduced through the valve inlet 735 at sufficient pressure to open the valve and allow the substance to flow through the valve and into the interior chamber 722 of the vial. Then, in order to withdraw substance from the vial assembly, a syringe (not shown) is connected to the flange 728 of the vial hub 724. This, in turn, causes the end surface of the syringe to engage and axially depress the rigid vial member 720 through the aperture 743. When the syringe is fully connected to the vial, the rigid valve member 720 is forced inwardly a sufficient distance to, in turn, force the sealing/connection member through the inner end of the aperture 743 and into the chamber 722. As a result, the rigid valve member 720 drops into the interior chamber 722 of the vial, and the syringe plunger then may be actuated to withdraw the substance from the vial into the syringe. The syringe is then disconnected from the vial and a needle (not shown) is attached to the connector of the syringe for injection into a patient. The empty vial 710 may then be disposed of.

One advantage of the container and valve assembly of the present is that it may be used to fill, store and/or dispense lyophilized medicaments or other substances. In order to fill the container with a lyophilized substance, after introduction of the substance from the filling member through the open valve assembly and into the chamber of the container, and with the valve member located in an open position, the chamber is evacuated. The chamber may be evacuated by placing the container, and preferably a plurality of containers mounted on a suitable first fixture for fixing the positions of the containers relative to each other, into a lyophilization station comprising a vacuum chamber of a type known to those of ordinary skill in the pertinent art. The lyophilization station is a station 79 located downstream of the filling station 77 in FIG. 9A. In the lyophilization station 79, a suitable second fixture is moved into engagement with the valve members of the vials to move the valve members into their open positions, the chamber is evacuated, and the medicament or other substance is then lyophilized in accordance with any of numerous different lyophilization processes that are currently known, or that later become known. After the substances in the vials are lyophilized, the second fixture is moved out of engagement with the valve members to, in turn, allow the valve members to close and seal the lyophilized substances within the evacuated chambers of the containers.

In use, a syringe may be connected to the mounting surface of a container to open the valve in the same manner as described above. Then, a diluent is injected from the syringe into the chamber, the diluent and lyophilized substances are mixed, and the mixture is then ready for injection.

As may be recognized by those of ordinary skill in the pertinent art based on the teachings herein, numerous changes may be made to the above-described and other embodiments of the present disclosure without departing from the scope of the invention as defined in the appended claims. For example, the components of the vial may be made of any of numerous different materials that are currently known, or later become known for performing the functions of the various components. The valve assembly may take any of numerous different configurations that are currently known, or later become known for performing the functions of the different valve assemblies described herein. Similarly, the vial may take any of numerous different shapes and configurations that are currently or later become known. Also, the form and configuration of any of the components of the sterile filling assembly disclosed herein may be changed, or any number of stations may be added to the sterile filling assembly to provide additional functionality. In addition, the containers may take the form of any of numerous different vials, syringes or other containers or dispensers. Further, the principles of the present invention are equally applicable to containers other than vials, and may be applied, for example, to any of numerous different containers for storing and dispensing different substances. Accordingly, this detailed description of embodiments is to be taken in an illustrative as opposed to a limiting sense.

What is claimed is:

1. A method comprising the following steps:
    filling a sealed empty sterile device including a body defining a chamber, and a sealing portion forming a liquid-tight seal between the chamber and ambient atmosphere, wherein the filling step comprises sterile filling a liquid substance to be lyophilized through the sealing portion and into the sealed, empty, sterile chamber;
    evacuating the chamber through a fluid passageway formed in the sealing portion;
    lyophilizing the substance within the evacuated chamber; and
    closing the fluid passageway through the sealing portion and hermetically sealing the lyophilized substance within the chamber.

2. A method as defined in claim 1, wherein the closing step occurs after the lyophilizing step.

3. A method as defined in claim 1, further comprising the step of sterilizing the sealed empty device.

4. A method as defined in claim 3, wherein the sterilizing step includes irradiating the sealed empty device.

5. A method as defined in claim 4, wherein the step of irradiating the sealed empty device includes subjecting the device to at least one of gamma, e-beam and laser radiation.

6. A method as defined in claim 1, wherein the device includes a valve assembly coupled in fluid communication with the chamber and defining (i) an open position permitting at least one of (a) passage of the substance through the valve assembly and into the chamber, and (b) passage of fluid out of the chamber; and (ii) a closed position forming a fluid-tight seal between the chamber and ambient atmosphere, wherein the method comprises the following steps: sterilizing the sealed empty device; filling the sterilized empty device with the substance by moving at least one of the valve assembly and a filling or injection member into engagement with the other; introducing substance from the filling or injection member through the valve assembly and into the chamber; and moving at least one of the valve assembly and filling or injection member relative to the other to disengage the valve assembly and filling or injection member.

7. A method as defined in claim 6, wherein the valve assembly extends through the sealing portion.

8. A method as defined in claim 6, wherein the valve assembly includes a flexible valve member defining a spring that is approximately dome-shaped when the valve assembly is in the closed position.

9. A method as defined in claim 1, wherein the device includes a valve assembly including a valve seat, and a flexible valve member overlying the valve seat and forming a normally closed interface defining a fluid-tight seal between the valve member and the valve seat, wherein the method further comprises the following steps:

filling the sterile empty chamber with the substance by moving at least one of the valve assembly and a filling or injection member into fluid communication with the other;

introducing the substance from the filling or injection member at sufficient pressure into the interface between the valve member and the valve seat to move the valve member relative to the valve seat and flow through the interface between the valve member and the valve seat and into the chamber;

terminating the flow of the substance from the filling or injection member into the interface between the valve member and the valve seat, allowing the flexible valve member to form the normally closed interface defining the fluid-tight seal between the valve member and the valve seat, and sealing the substance with the chamber; and moving at least one of the valve assembly and the filling or injection member relative to the other to disconnect the valve assembly and the filling or injection member from fluid communication with each other.

10. A method as defined in claim 9, wherein the device further includes an outlet valve that is normally closed and forms a fluid-tight seal between the chamber and ambient atmosphere; and further comprising the step of dispensing substance from the chamber through the outlet valve.

11. A method as defined in claim 10, wherein the dispensing step includes dispensing multiple doses of the substance from the chamber through the outlet valve, and maintaining the substance remaining within the chamber sterile and sealed within the chamber with respect to the ambient atmosphere.

12. A method as defined in claim 11, further comprising the step of connecting the device to a syringe, injecting a diluent from the syringe into the chamber, and mixing the lyophilized substance with the diluent within the chamber.

13. A method as defined in claim 6, further comprising the step of connecting the device to a syringe, moving the valve assembly from the closed to the open position, injecting a diluent from the syringe into the chamber, and mixing the lyophilized substance with the diluent within the chamber.

14. A lyophilization device comprising a body defining a sealed, empty sterile chamber, and a sealing portion forming a liquid-tight seal between the chamber and ambient atmosphere, wherein the sealing portion is configured and adapted for sterile filling a liquid substance to be lyophilized through the sealing portion and into the sealed, empty, sterile chamber, forming a fluid passageway through the sealing portion and evacuating the chamber through the fluid passageway of the sealing portion, lyophilizing the substance within the evacuated chamber, and closing the fluid passageway through the sealing portion and hermetically sealing the lyophilized substance within the chamber.

15. A lyophilization device as defined in claim 14, further comprising a one-way valve defining the fluid passageway.

16. A lyophilization device as defined in claim 15, wherein the one-way valve extends through the sealing portion.

17. A lyophilization device as defined in claim 14, wherein the device includes a vial defining the body and the chamber within the body, the body defines an opening, and the sealing portion defines a stopper sealingly engaging the opening to form the liquid-tight seal between the chamber and the ambient atmosphere.

18. A lyophilization device as defined in claim 15, wherein the one-way valve defines (i) an open position permitting at least one of (a) passage of the substance through the one-way valve and into the chamber, and (b) passage of fluid out of the chamber; and (ii) a closed position forming a fluid-tight seal between the chamber and ambient atmosphere.

19. A lyophilization device as defined in claim 18, wherein the one-way valve includes a flexible valve member defining a spring that is approximately dome-shaped when the one-way valve is in the closed position.

20. A lyophilization device as defined in claim 15, wherein the one-way valve includes a valve seat, and a flexible valve member overlying the valve seat and forming a normally closed interface defining a fluid-tight seal between the valve member and the valve seat.

21. A lyophilization device as defined in claim 20, further including an outlet valve that is normally closed and forms a fluid-tight seal between the chamber and ambient atmosphere, and is adapted to dispense the substance therethrough.

22. A method as defined in claim 1, wherein the device includes a vial defining the body and the chamber within the body, the body defines an opening, and the sealing portion defines a stopper sealingly engaging the opening to form the liquid-tight seal between the chamber and the ambient atmosphere.

23. A method as defined in claim 1, further comprising the step of forming the fluid passageway through the sealing portion.

24. A lyophilization device as defined in claim 18, further comprising a filling assembly including a filling member engageable with the one-way valve and coupleable in fluid communication with a substance source for introducing the substance through the one-way valve, wherein at least one of the one-way valve and the filling member is movable relative to the other to move the valve between the closed and open positions and introduce the substance from the filling member through the one-way valve.

25. A system comprising:
a valve assembly defining (i) an open position permitting passage of substance therethrough, and (ii) a closed position preventing passage of substance therethrough and forming a fluid-tight seal between an inlet end and an outlet end thereof, the valve assembly comprising a flexible valve member defining a spring that is approximately dome-shaped when the valve assembly is in the closed position; and a filling assembly including a filling member engageable with the valve assembly and coupleable in fluid communication with a substance source for introducing the substance through the valve assembly, wherein at least one of the valve assembly and the filling member is movable relative to the other to move the valve assembly between the closed and open positions and introduce the substance from the filling member through the valve assembly.

26. A system as defined in claim 25, wherein the valve assembly further includes a valve seat, and the flexible valve member is movable between the open position spaced away from the valve seat and the closed position engaging the valve seat.

27. A system as defined in claim 26, wherein the flexible valve member defines a sealing surface engageable with the valve seat for forming a fluid-tight seal therebetween when in the closed position.

28. A system as defined in claim 25, wherein the spring stores energy therein upon moving the valve member from the closed to the open position, and applies said stored energy to in turn move the valve member from the open to the closed position.

29. A system as defined in claim 25, wherein the flexible valve member defines at least one aperture therein for permitting the flow of substance therethrough in the open position.

30. A system as defined in claim 25, wherein the valve assembly is coupled in fluid communication with a chamber, where in the open position the valve assembly permits at least one of (a) passage of substance through the valve assembly and into the chamber, and (b) passage of substance out of the chamber for dispensing the substance therefrom, and in the closed position the valve assembly forms a fluid-tight seal between the chamber and an exterior of the valve assembly; and the filling assembly is engageable with the valve assembly for introducing the substance through the valve assembly and into the chamber.

31. A system as defined in claim 30, further comprising a body including the chamber therein.

32. An system as defined in claim 31, wherein the body defines a lyophilization device.

33. A system as defined in claim 25, wherein the filling member is coupled in fluid communication with a substance source.

34. A system as defined in claim 25, wherein the spring normally biases the flexible valve member into the closed position.

35. A method comprising the following steps:

engaging a valve assembly and a filling assembly with each other, the valve assembly defining (i) an open position permitting passage of substance therethrough, and (ii) a closed position preventing passage of substance therethrough and forming a fluid-tight seal between an inlet end and an outlet end thereof, and comprising a flexible valve member defining a spring that is approximately dome-shaped when the valve assembly is in the closed position; and the filling assembly including a filling member engageable with the valve assembly and coupleable in fluid communication with a substance source for introducing the substance through the valve assembly, opening the valve assembly from the closed positions into the open position; and introducing substance from the filling member through the open valve assembly.

36. A method as defined in claim 35, further comprising coupling the filling assembly in fluid communication with a substance source, wherein the introducing step includes introducing substance from the substance source through the filling member and through the open valve assembly.

37. A method as defined in claim 35, wherein the valve assembly further includes a valve seat, the flexible valve member engages the valve seat in the closed position and is spaced away from the valve seat in the open position, and the step of opening the valve assembly includes moving the flexible valve member from the closed position engaging the valve seat to the open position spaced away from the valve seat.

38. A method as defined in claim 35, wherein the valve assembly is in fluid communication with a chamber and the introducing step includes introducing substance from the filling member into the chamber through the open valve assembly.

39. A method as defined in claim 35, further comprising disengaging the valve assembly and the filling assembly from each other, and, in turn, closing the valve assembly from the open position into the closed position.

* * * * *